(12) United States Patent
Nagao et al.

(10) Patent No.: US 8,729,530 B2
(45) Date of Patent: May 20, 2014

(54) MATERIAL FOR LIGHT-EMITTING DEVICE AND LIGHT-EMITTING DEVICE

(75) Inventors: Kazumasa Nagao, Otsu (JP); Seiichiro Murase, Otsu (JP)

(73) Assignee: Toray Industries, Inc., Tokyo (JP)

( * ) Notice: Subject to any disclaimer, the term of this patent is extended or adjusted under 35 U.S.C. 154(b) by 704 days.

(21) Appl. No.: 12/308,374

(22) PCT Filed: Jun. 8, 2007

(86) PCT No.: PCT/JP2007/061597
§ 371 (c)(1),
(2), (4) Date: Dec. 12, 2008

(87) PCT Pub. No.: WO2007/145136
PCT Pub. Date: Dec. 21, 2007

(65) Prior Publication Data
US 2010/0163852 A1 Jul. 1, 2010

(30) Foreign Application Priority Data

Jun. 15, 2006 (JP) .................................. 2006-165634
Jul. 14, 2006 (JP) .................................. 2006-193736

(51) Int. Cl.
*H01L 51/54* (2006.01)

(52) U.S. Cl.
USPC ...................................... 257/40; 257/E51.05

(58) Field of Classification Search
USPC ........... 257/40, E51.049, E51.05; 543/26, 38; 562/470–471
See application file for complete search history.

(56) References Cited

U.S. PATENT DOCUMENTS

| | | | | |
|---|---|---|---|---|
| 5,817,431 A * | 10/1998 | Shi et al. | ........................ | 428/690 |
| 6,767,654 B2 | 7/2004 | Tamao et al. | .................. | 428/690 |
| 2003/0068524 A1 | 4/2003 | Hatwar | ........................ | 428/690 |
| 2004/0058194 A1 | 3/2004 | Stossel et al. | .................. | 428/690 |
| 2005/0238920 A1 | 10/2005 | Sotoyama et al. | ............ | 428/690 |
| 2007/0072002 A1 | 3/2007 | Kim et al. | ...................... | 428/690 |
| 2009/0066245 A1 | 3/2009 | Sugimoto et al. | ............. | 313/540 |
| 2009/0096356 A1 | 4/2009 | Murase et al. | ................. | 313/504 |

FOREIGN PATENT DOCUMENTS

| | | |
|---|---|---|
| EP | 1 217 668 A1 | 6/2002 |
| EP | 1 345 278 A2 | 9/2003 |
| EP | 1 816 114 A1 | 8/2007 |
| EP | 1 905 754 A1 | 4/2008 |
| JP | 5-017765 A | 1/1993 |
| JP | 5-021161 A | 1/1993 |
| JP | 10-340786 A | 12/1998 |
| JP | 2000-260565 A | 9/2000 |
| JP | 2000-268961 A | 9/2000 |
| JP | 2000-290645 A | 10/2000 |
| JP | 2000-294373 A | 10/2000 |
| JP | 2000294373 A * | 10/2000 |
| JP | 2001-093670 A | 4/2001 |
| JP | 2001-118682 A | 4/2001 |
| JP | 2001-291590 A | 10/2001 |
| JP | 2003-086380 A | 3/2003 |
| JP | 2003-142263 A | 5/2003 |
| JP | 2003-272864 A | 9/2003 |

(Continued)

OTHER PUBLICATIONS

English translation of JP 2000294373 downloaded May 12, 2011.*
Supplementary European Search Report dated Jun. 17, 2010, issued in European Patent Application No. 07767065.1-1218/2028249 (PCT/JP2007/061597).
Tang, C.W. et al., "organic electroluminescent diodes", Applied Physics Letters, vol. 51, No. 12, pp. 913-915 (1987).

(Continued)

*Primary Examiner* — Thomas L Dickey
(74) *Attorney, Agent, or Firm* — Kubovcik & Kubovcik

(57) ABSTRACT

The present invention provides a light emitting device material which enables a light emitting device having high efficiency and excellent chromatic purity and durability using a light emitting device material containing a pyrene compound represented by formula (1), wherein any one of $R^1$ to $R^{10}$ is a group represented by formula (2), or 1 to 4 substituents is/are group(s) represented by formula (3), and a light emitting device using the same.

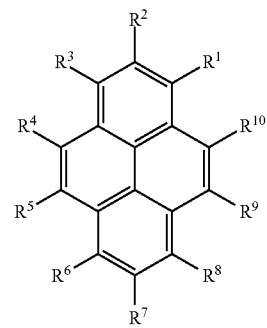

(1)

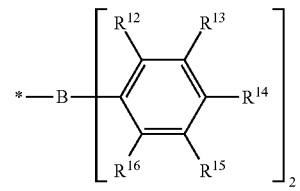

(2)

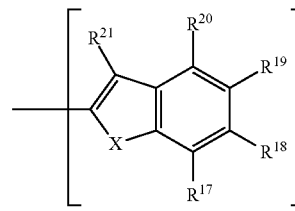

(3)

18 Claims, 1 Drawing Sheet

(56) References Cited

FOREIGN PATENT DOCUMENTS

| | | | |
|---|---|---|---|
| JP | 2005-501372 A | 1/2005 | |
| JP | 2005-047868 A | 2/2005 | |
| JP | 2005-317314 A | 11/2005 | |
| JP | 2005317314 A | * 11/2005 | |
| JP | 2006-176491 A | 7/2006 | |
| JP | 2007-015961 A | 1/2007 | |
| JP | 2007-84828 A | 4/2007 | |
| WO | 00/40586 A1 | 7/2000 | |
| WO | 2006/057326 A1 | 6/2006 | |
| WO | WO 2006057325 A1 * | 6/2006 | ............ H05B 33/26 |
| WO | WO 2006057326 A1 * | 6/2006 | |
| WO | 2007/004364 A1 | 1/2007 | |

OTHER PUBLICATIONS

Communication pursuant to Article 94(3) datedMay 24, 2011, issued in European Patent Application No. 07767065.1-1218/2028249.

* cited by examiner

MATERIAL FOR LIGHT-EMITTING DEVICE AND LIGHT-EMITTING DEVICE

This application is a 371 of international application PCT/JP2007/061597, filed Jun. 8, 2008, which claims priority based on Japanese patent application Nos. 2006-165634 and 2006-193736 filed Jun. 15, 2006, and Jul. 14, 2006, respectively, which are incorporated herein by reference.

TECHNICAL FIELD

The present invention relates to a light emitting device material which is useful as a fluorescent dye and a charge transporting material, and a light emitting device using the same. The light emitting device of the present invention can be used for display elements, flat panel displays, back lights, lighting, interiors, signs, signboards, electronic cameras, light signal generators and the like.

BACKGROUND ART

There has recently been considerable research into organic thin-film light emitting devices which emit light when electrons injected from a cathode and holes injected from an anode recombine within an organic fluorescent body interposed between the cathode and the anode. Such light emitting devices are a focus of attention on account of their characteristics of thin shape, high luminance at a low driving voltage and polychromic light emission based on suitable selection of the fluorescent materials.

Numerous research organizations have been carrying out such research since C. W. Tang and co-workers at Kodak first described the fact that an organic thin-film light emitting device emits light of high luminance. A typical organic thin-film light emitting element construction proposed by the Kodak research group is that in which there are provided, in turn, on an ITO glass substrate, a hole transporting diamine compound, tris (8-hydroxyquinolate)aluminum(III) as the emissive layer and Mg:Ag (alloy) as the cathode. A 1,000 cd/m² green colored light emission is possible at a driving voltage of about 10 V (refer to Non-Patent Document 1).

It has intensively been studied to apply the organic thin-film light emitting device as a display since various luminescent colors can be obtained by using various luminescence materials in the emissive layer. Research on the use of a green emissive material as a primary-color emissive material is at the most advanced stage and intensive study is being performed so as to improve characteristics of a red emissive material and a blue emissive material.

One of largest problems associated with organic thin-film light emitting devices is to reconcile the luminance efficiency, chromatic purity and durability of the device. In particular, there are few blue emissive materials which provide a device which has excellent chromatic purity and durability and, at the same time, reliability. For example, there is disclosed a technique of using a styrylamine derivative (refer to Patent Document 1), a perylene derivative (refer to Patent Document 2) and an anthracene derivative (refer to Patent Document 3) as a blue guest material. There is also disclosed a technique of using a pyrene compound in a blue light emitting device (refer to Patent Documents 4, 5). There is also reported an example in which a compound (refer to Patent Documents 6 to 8) having a pyrene skeletal structure containing a diarylboryl group introduced therein is used in a light emitting device. However, all of the resultant devices had insufficient chromatic purity and durability.

[Patent Document 1]
  Japanese Unexamined Patent Publication (Kokai) No. 5-17765
[Patent Document 2]
  Japanese Unexamined Patent Publication (Kokai) No. 2003-86380
[Patent Document 3]
  International Publication No. WO 00/40586 Pamphlet
[Patent Document 4]
  Japanese Unexamined Patent Publication (Kokai) No. 5-21161
[Patent Document 5]
  Japanese Unexamined Patent Publication (Kokai) No. 2001-118682
[Patent Document 6]
  Japanese Unexamined Patent Publication (Kokai) No. 2000-294373
[Patent Document 7]
  Japanese Unexamined Patent Publication (Kokai) No. 2000-290645
[Patent Document 8]
  Kohyo (National Publication of Translated Version) No. 2005-501372
[Non-Patent Document 1]
  Applied Physics Letters (USA) 1987, Vol. 51, No. 12, pp. 913-915

DISCLOSURE OF THE INVENTION

Thus, an object of the present invention is to solve these problems in the prior art by providing a light emitting device material which enables a light emitting device having high luminance efficiency and excellent chromatic purity and durability, and a light emitting device using the same.

The present invention provides (1) A light emitting device material containing a pyrene compound represented by the general formula (1):

[Chemical Formula 1]

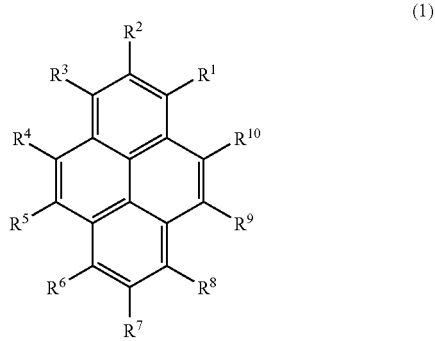

(1)

wherein $R^1$ to $R^{10}$ may be the same or different and represent a group selected from the group consisting of hydrogen, an alkyl group, a cycloalkyl group, a heterocyclic group, an alkenyl group, a cycloalkenyl group, an alkynyl group, an alkoxy group, an alkylthio group, an arylether group, an arylthioether group, an aryl group, a heteroaryl group, halogen, an amino group, a cyano group, a silyl group and —P(=O)—$R^{11}$, and adjacent substituents may be combined to form a ring structure; $R^{11}$ represents a group selected from among an aryl group and a heteroaryl group, provided that any one of $R^1$ to $R^{10}$ is a group represented by the following general formula (2) or 1 to 4 substituents is/are group(s) represented by the following general formula (3) below:

[Chemical Formula 2]

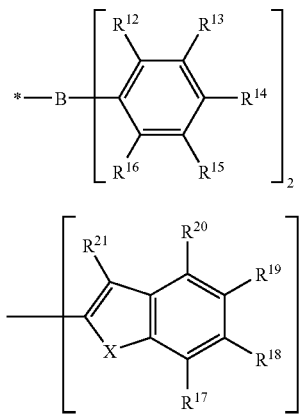

wherein $R^{12}$ to $R^{21}$ may be the same or different and represent a group selected from the group consisting of hydrogen, an alkyl group, a cycloalkyl group, a heterocyclic group, an alkenyl group, a cycloalkenyl group, an alkynyl group, an alkoxy group, an alkylthio group, an arylether group, an arylthioether group, an aryl group, a heteroaryl group, halogen, an amino group, a cyano group and a silyl group, and adjacent substituents may be combined to form a ring structure, B is a boron atom, X is a group selected from among an oxygen atom, a sulfur atom and $—NR^{22}—$, $R^{22}$ is a group selected from among hydrogen, an alkyl group, a cycloalkyl group, a heterocyclic group, an alkenyl group, a cycloalkenyl group, an alkynyl group, an aryl group, a heteroaryl group and an amino group, and $R^{22}$ and $R^{17}$ may be combined to form a ring.

The present invention also provides a light emitting device comprising at least an anode, a cathode and an emissive layer, and the emissive layer exists between the anode and the cathode, the emissive layer emitting light by means of electrical energy, and the emissive layer contains a pyrene compound represented by the general formula (1).

Effect of the Invention

The light emitting device material of the present invention material can provide a light emitting device material having high light emitting performance which can be used for a light emitting device. According to the present invention, a light emitting device having high luminance efficiency and excellent chromatic purity and durability can be obtained.

BEST MODE FOR CARRYING OUT THE INVENTION

Figure 1:
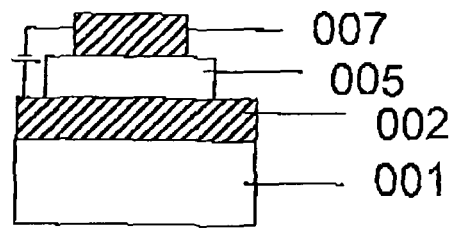
FIG. 1 illustrates a first embodiment of the light emitting device according to the present invention.

The pyrene compound represented by the general formula (1) will be described in detail below:

[Chemical Formula 3]

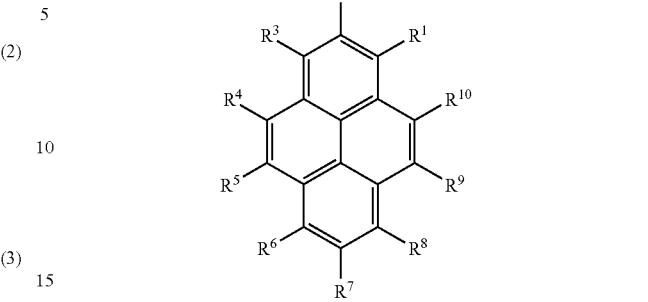

wherein $R^1$ to $R^{10}$ may be the same or different and represent a group selected from the group consisting of hydrogen, an alkyl group, a cycloalkyl group, a heterocyclic group, an alkenyl group, a cycloalkenyl group, an alkynyl group, an alkoxy group, an alkylthio group, an arylether group, an arylthioether group, an aryl group, a heteroaryl group, halogen, an amino group, a cyano group, a silyl group and $—P(=O)—R^{11}$, and adjacent substituents may be combined to form a ring structure; $R^{11}$ represents a group selected from among an aryl group and a heteroaryl group, However any one of $R^1$ to $R^{10}$ is a group represented by the following general formula (2) or 1 to 4 substituents is/are group(s) represented by the following general formula (3):

[Chemical Formula 4]

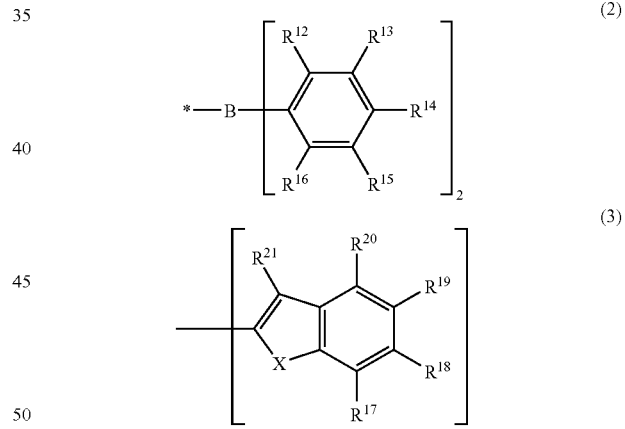

wherein $R^{12}$ to $R^{21}$ may be the same or different and represent a group selected from the group consisting of hydrogen, an alkyl group, a cycloalkyl group, a heterocyclic group, an alkenyl group, a cycloalkenyl group, an alkynyl group, an alkoxy group, an alkylthio group, an arylether group, an arylthioether group, an aryl group, a heteroaryl group, halogen, an amino group, a cyano group and a silyl group, and adjacent substituents may be combined to form a ring structure, B is a boron atom, X is a group selected from among an oxygen atom, a sulfur atom and $—NR^{22}—$, $R^{22}$ is a group selected from among hydrogen, an alkyl group, a cycloalkyl group, a heterocyclic group, an alkenyl group, a cycloalkenyl group, an alkynyl group, an aryl group, a heteroaryl group and an amino group, and $R^{22}$ and $R^{17}$ may be combined to form a ring.

Among these substituents, the alkyl group means a saturated aliphatic hydrocarbon group such as a methyl group, an ethyl group, an n-propyl group, an isopropyl group, an n-butyl group, a sec-butyl group or a tert-butyl group with or without substituents. There is no limitation on additional substituents when substituted, and examples thereof include an alkyl group, an aryl group and a heteroaryl group. These comments shall apply in the following description. There is no limitation on the carbon number of the alkyl group. In view of availability and cost, the alkyl group preferably has 1 or more and 20 or less carbon atoms, and more preferably 1 or more and 8 or less carbon atoms, The cycloalkyl group means a saturated alicyclic hydrocarbon group such as cyclopropyl, cyclohexyl, norbornyl or adamantyl with or without substituents. There is no limitation on the carbon number of the cycloalkyl group. The cycloalkyl group preferably has 3 or more and 20 or less carbon atoms.

The heterocyclic group means an aliphatic ring having an atom other than a carbon atom in the ring, such as a pyran ring, a piperidine ring or a cyclic amide with or without substituents. There is no limitation on the carbon number of the heterocyclic group. The heterocyclic group preferably has 2 or more and 20 or less carbon atoms.

The alkenyl group means an unsaturated aliphatic hydrocarbon group containing a double bond, such as a vinyl group, an allyl group or a butadienyl group with or without substituents. There is no limitation on the carbon number of the alkenyl group. The alkenyl group preferably has 2 to 20 carbon atoms.

The cycloalkenyl group means an unsaturated aliphatic hydrocarbon group containing a double bond, such as a cyclopentenyl group, a cyclopentadienyl group or a cyclohexenyl group with or without substituents. There is no limitation on the carbon number of the cycloalkenyl group. The cycloalkenyl group preferably has 3 or more and 20 or less carbon atoms.

The alkynyl group means an unsaturated aliphatic hydrocarbon group containing a triple bond, such as an ethynyl group with or without substituents. There is no limitation on the carbon number of the alkynyl group. The alkynyl group preferably has 2 to 20 carbon atoms.

The alkoxy group means a functional group bonded with an aliphatic hydrocarbon group via an ether bond, such as a methoxy group, an ethoxy group or a propoxy group, and the aliphatic hydrocarbon group with or without substituents. There is no limitation on the carbon number of the alkoxy group. The alkoxy group preferably has 1 or more and 20 or less carbon atoms.

The alkylthio group is a group in which an oxygen atom of an ether bond of an alkoxy group is substituted with a sulfur atom. A hydrocarbon group of the alkylthio group may have a substituent or not. There is no limitation on the carbon number of the alkylthio group. The alkylthio group preferably has 1 or more and 20 or less carbon atoms.

The arylether group means a functional group bonded with an aromatic hydrocarbon group via an ether bond, such as a phenoxy group, and the aromatic hydrocarbon group with or without substituents. There is no limitation on the carbon number of the arylether group. The arylether group preferably has 6 or more and 40 or less carbon atoms.

The arylthioether group is a group in which an oxygen atom of an ether bond of an arylether group is substituted with a sulfur atom. An aromatic hydrocarbon group in the arylether group may have a substituent or not. There is no limitation on the carbon number of the arylthioether group. The arylthioether group preferably has 6 or more and 40 or less carbon atoms.

The aryl group means an aromatic hydrocarbon group such as a phenyl group, a naphthyl group, a biphenyl group, a phenanthryl group, a terphenyl group or a pyrenyl group. The aryl group may have a substituent or not. There is no limitation on the carbon number of the aryl group. The aryl group preferably has 6 to 40 carbon atoms.

The heteroaryl group means a cyclic aromatic group having one or plural atom(s) other than a carbon atom in the ring, such as a furanyl group, a thiophenyl group, a pyrrolyl group, a benzofuranyl group, a benzothiophenyl group, an indolyl group, a pyridyl group or a quinolinyl group with or without substituents. There is no limitation on the carbon number of the heteroaryl group. The heteroaryl group preferably has 2 to 30 carbon atoms.

The halogen atom means fluorine, chlorine, bromine and iodine.

The amino group, the cyano group and —P(=O)—$R^{11}$ may have a substituent or not. Examples of substituents include alkyl, cycloalkyl, aryl and heteroaryl groups described above.

$R^{11}$ is a group selected from among an aryl group and a heteroaryl group.

The silyl group means a functional group having a bond to a silicon atom, such as a trimethylsilyl group, with or without substituents. There is no limitation on the carbon number of the silyl group. The silyl group preferably has 3 to 20 carbon atoms. And the silyl group preferably has 1 to 6 silicon atoms.

Optional adjacent two substituents (for example, $R^1$ and $R^2$ of the general formula (1)) may be combined with each other to form a conjugated or non-conjugated fused ring. A constituent element of the fused ring may contain an element selected from among nitrogen, oxygen, sulfur, phosphorus and silicon. The fused ring may be fused with another ring.

In a first aspect of the pyrene compound in the present invention, the pyrene compound has a pyrene skeletal structure and one diarylboryl group of the general formula (2) as an electron-accepting boron compound in the molecule. A light emitting device material containing a pyrene compound has high luminance efficiency and excellent durability.

When two or more of diarylboryl groups represented by the general formula (2) are introduced, heat resistance deteriorates and decomposition may occur when a film is formed by vacuum deposition. Therefore, it is preferred to introduce only one diarylboryl group represented by the general formula (2) to the pyrene skeletal structure so as to reconcile fluorescence quantum yield and heat resistance.

It is preferred that any one of $R^1$, $R^3$, $R^6$ and $R^8$ is a group represented by the general formula (2) and the substituent is bonded with the pyrene skeletal structure since fluorescence quantum yield is improved.

It is preferred that $R^{12}$, $R^{14}$ and $R^{16}$ are methyl groups since the vicinity of a boron atom will be made sterically bulky and thus the resultant compound is stable in the air and has excellent heat resistance.

In a second aspect of the pyrene compound in the present invention, the pyrene compound has 1 to 4 groups having a structure selected from a pyrene skeletal structure, an electron-donating fused aromatic benzofuran skeletal structure (when X is an oxygen atom) of the general formula (3) and a benzothiophene skeletal structure (when X is a sulfur atom) or an indole skeletal structure (when X is —NR$^{22}$—) in the molecule. It is preferred to have 1 to 4 groups represented by the general formula (3) since the pyrene compound is excellent in fluorescence quantum yield and chromatic purity. It is more preferred to have 1 to 2 groups represented by the general formula (3) since the pyrene compound is more excellent in fluorescence quantum yield and chromatic purity. A light emitting device material containing such a pyrene compound has high luminance efficiency and excellent chromatic purity.

It is preferred that at least one of R$^1$, R$^3$, R$^6$ and R$^8$ is a group represented by the general formula (3) and the substituent is bonded with a pyrene skeletal structure since fluorescence quantum yield is excellent. When the number of the group represented by the general formula (3) is 2 or more, it is more preferred that at least R$^1$ and R$^6$ are groups represented by the general formula (3).

It is particularly preferred that X is an oxygen atom in the general formula (3) since higher luminance efficiency than that in case of a sulfur atom and —NR$^{22}$— is obtained and Stokes' shift becomes narrower and also chromatic purity is excellent.

In any aspect, it is preferred that at least one of R$^1$ to R$^{10}$ is an alkyl group or an aryl group since concentration quenching caused by interaction between pyrene compounds is suppressed and high fluorescence quantum yield can be attained. It is more preferred that R$^1$ is a group represented by the general formula (2) or (3), R$^3$ is an alkyl group or an aryl group and R$^7$ is an alkyl group since excellent effect of inhibiting interaction between pyrene compounds is exerted and it becomes possible to emit light with high efficiency. It is also preferred that R$^1$ is a group represented by the general formula (2) or (3) and R$^6$ or R$^8$ is an alkyl group, an aryl group or a heteroaryl group since interaction between pyrene compounds is suppressed and it becomes possible to emit light with high efficiency. It is particularly preferred that R$^6$ or R$^8$ is an aryl group or a heteroaryl group since high fluorescence intensity is maintained at a solid or thin film state and it becomes possible to emit light with high efficiency. It is more preferred that both R$^3$ and R$^8$ are aryl or heteroaryl groups since a more excellent effect is exerted.

Specific examples of the pyrene compound include, but are not limited to, the following.

[Chemical Formula 5]

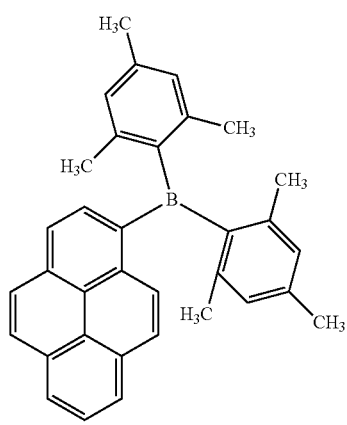

[1]

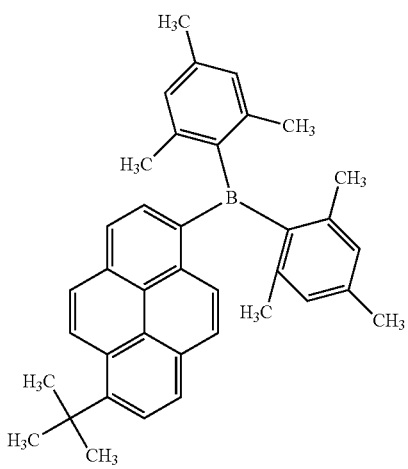

[2]

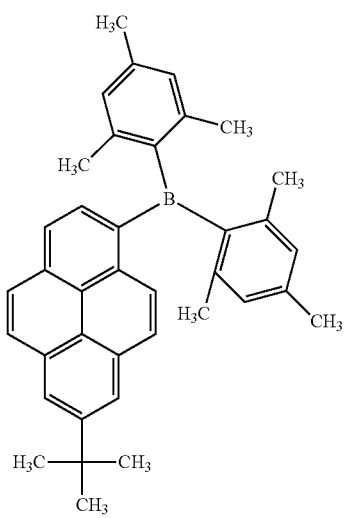

[3]

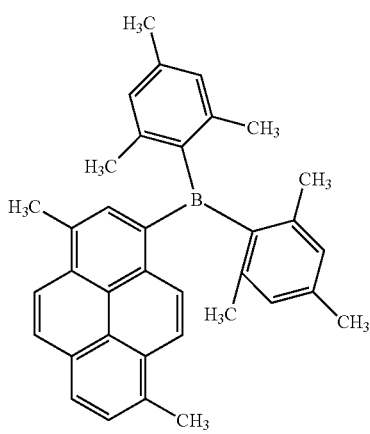

[4]

[5]
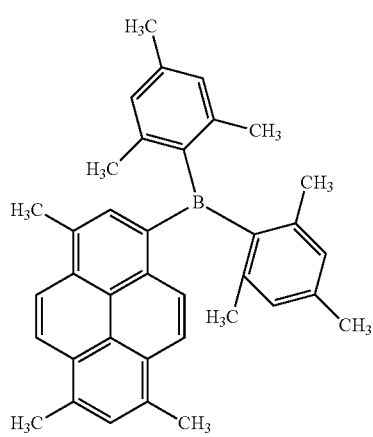
[6]
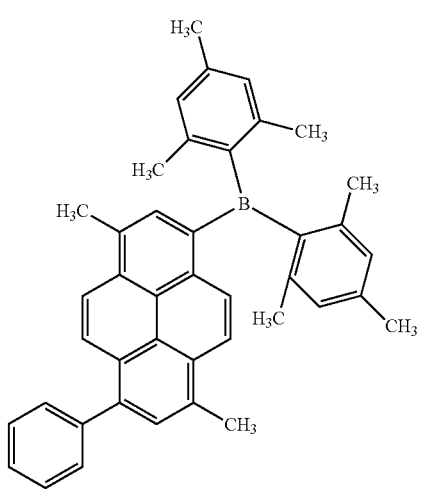
[7]
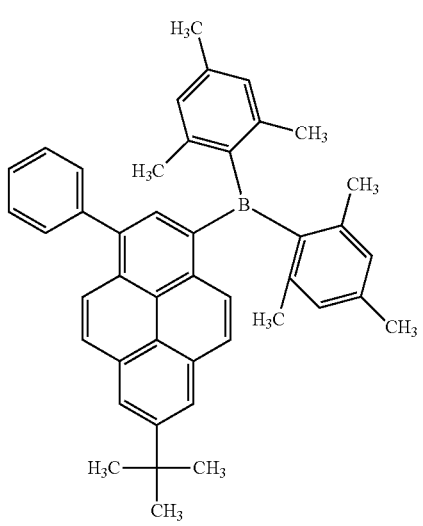
[8]
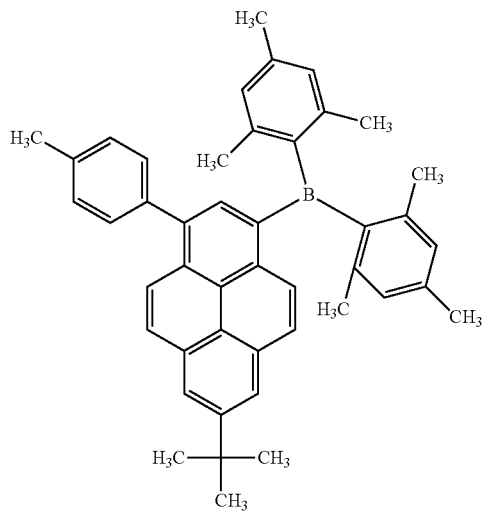
[9]
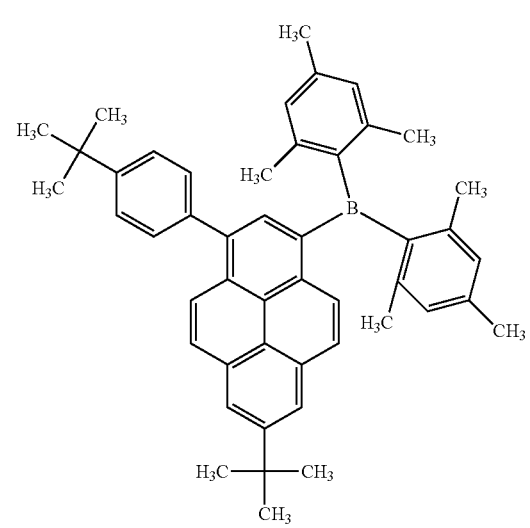
[10]
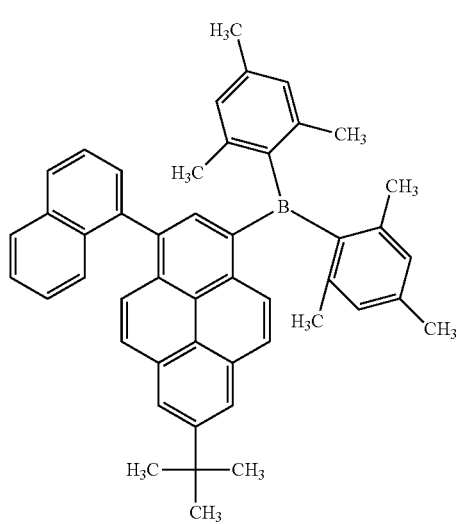

[11]
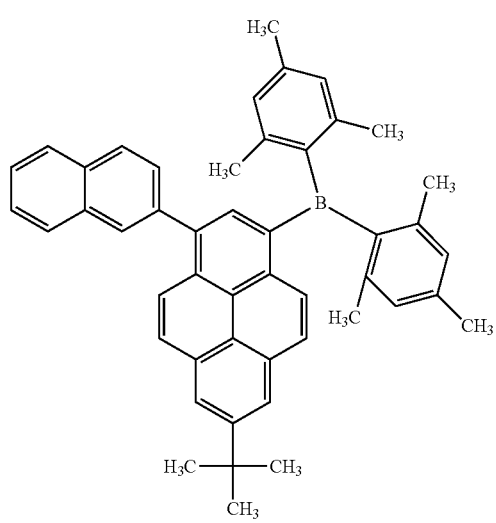
[12]
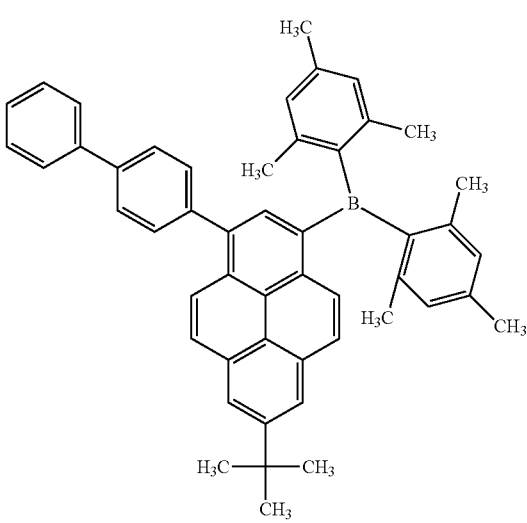
[Chemical Formula 6]
[13]
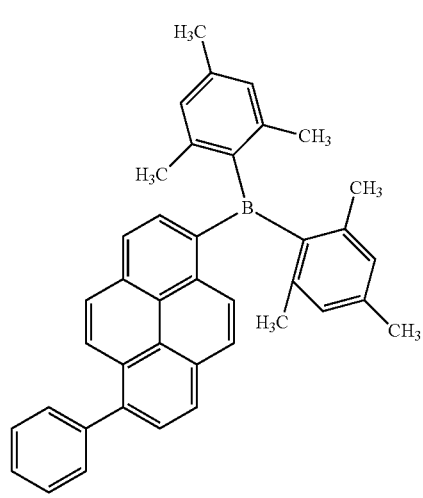
[14]
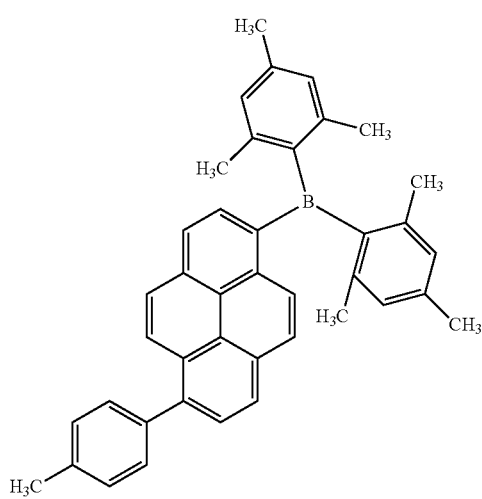
[15]
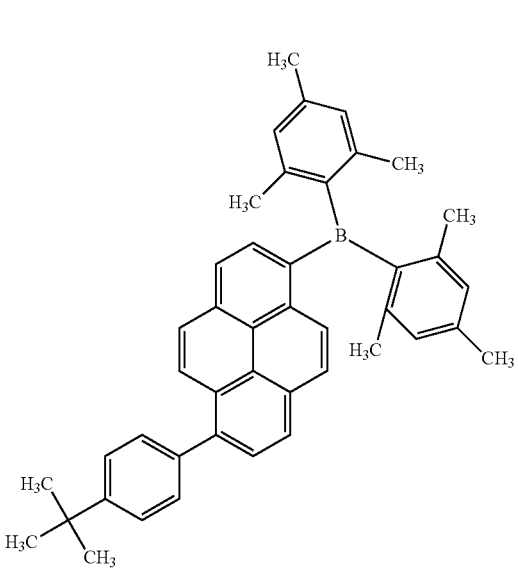
[16]
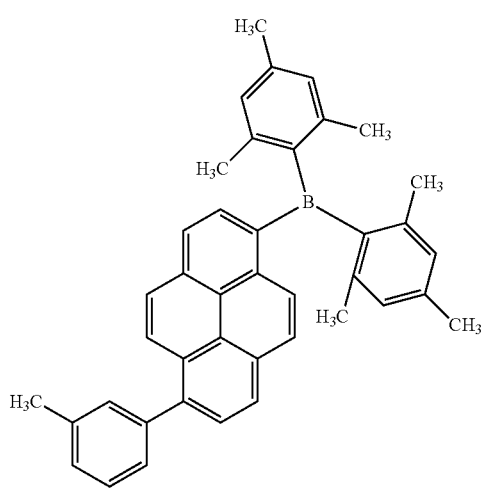

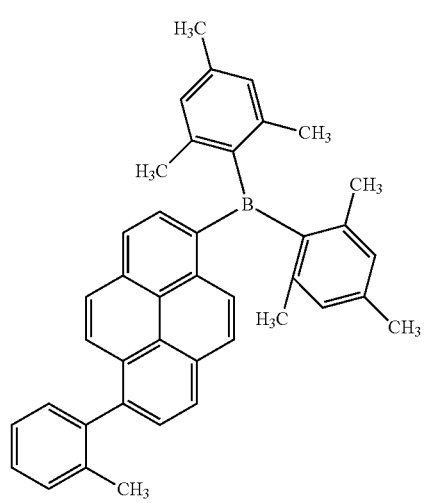
[17]
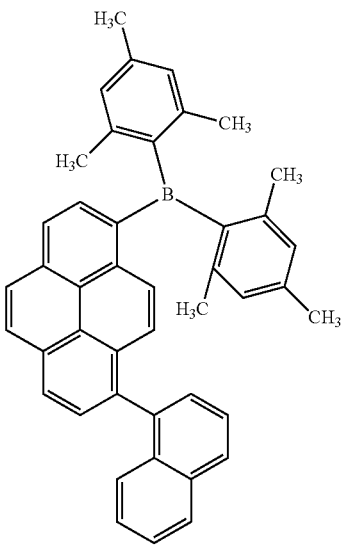
[20]
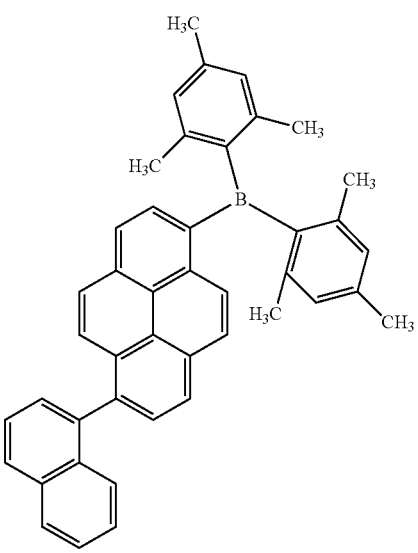
[18]
[21]
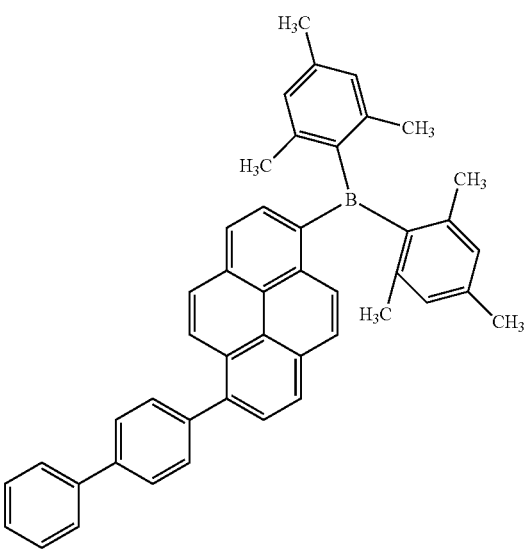
[19]
[22]

[23]
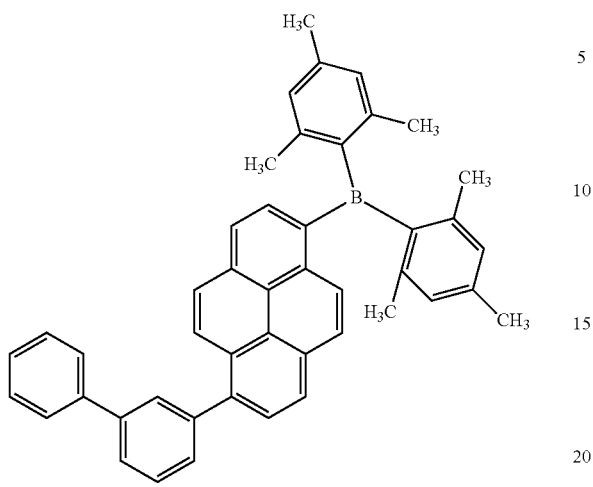
[24]
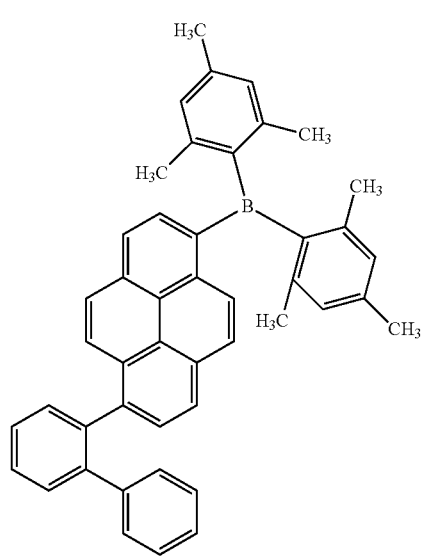
[Chemical Formula 7]
[25]
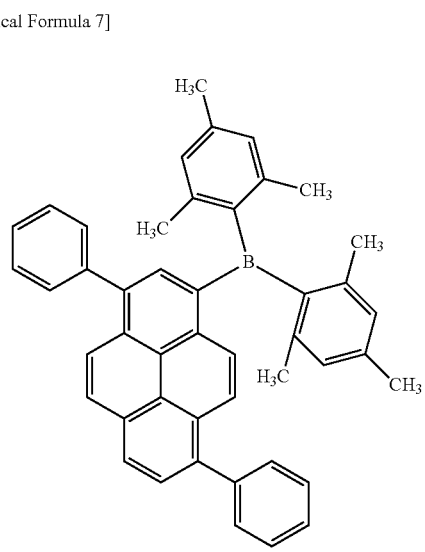
[26]
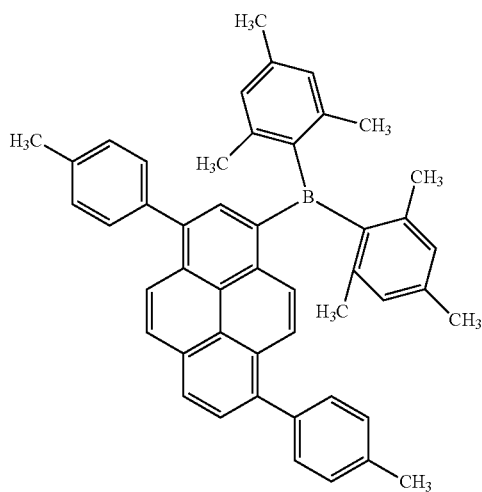
[27]
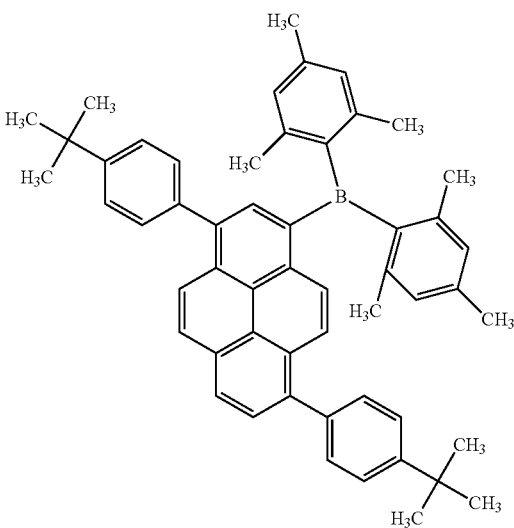
[28]
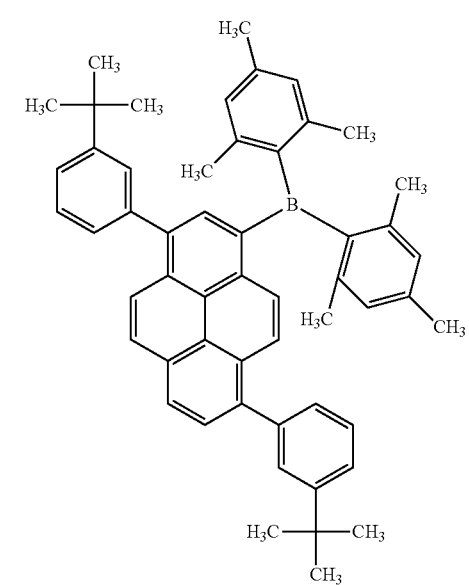

[29]
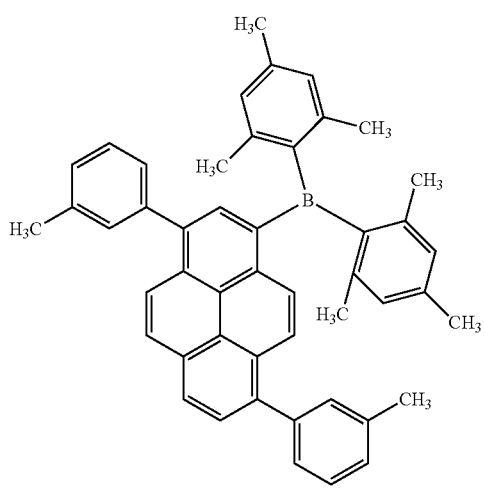
[30]
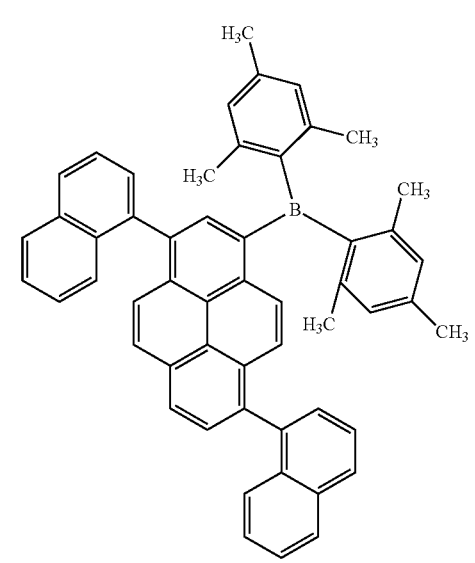
[31]
[32]
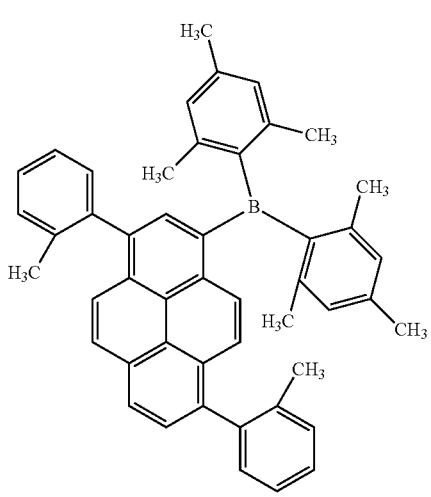
[33]
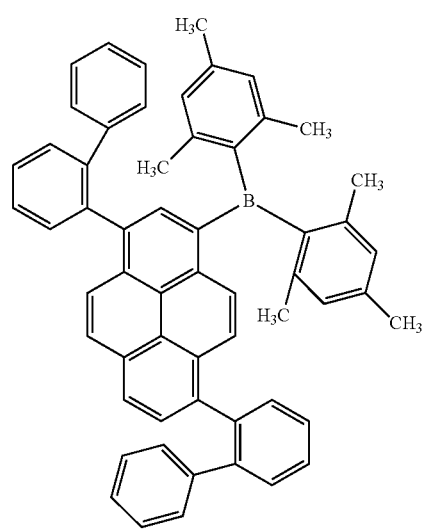
[34]
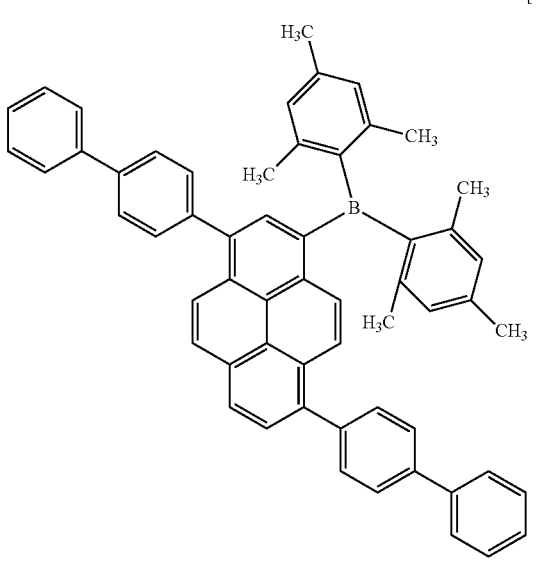

[35]
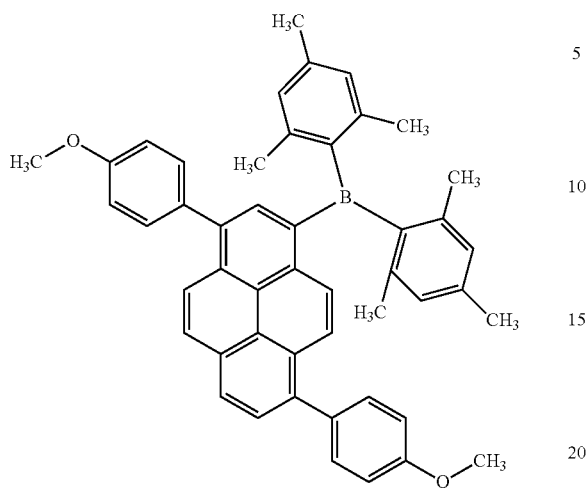
[Chemical Formula 8]
[36]
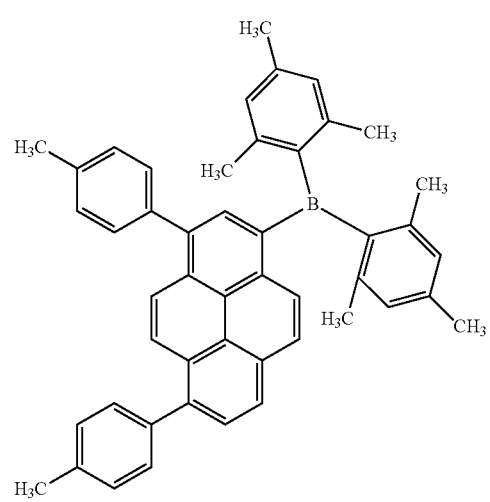
[37]
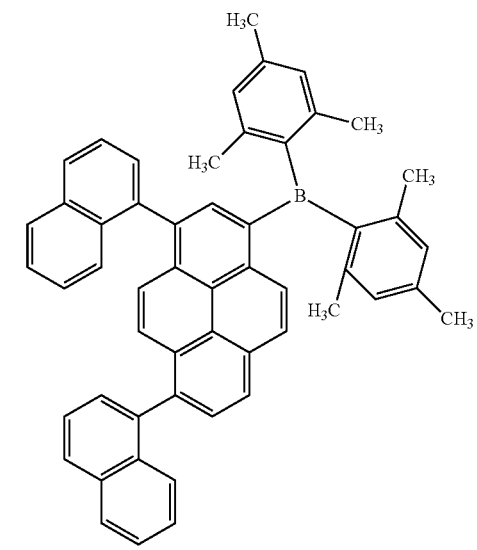
[38]
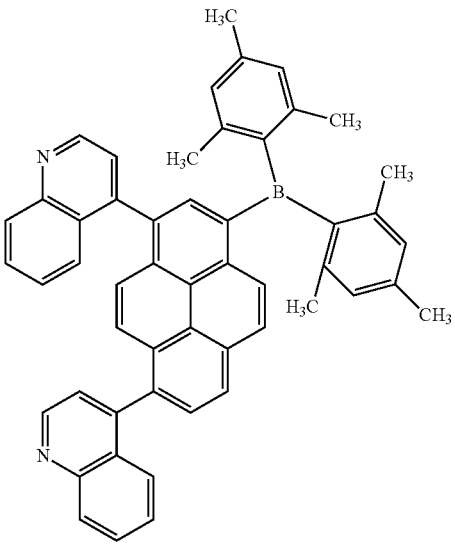
[39]
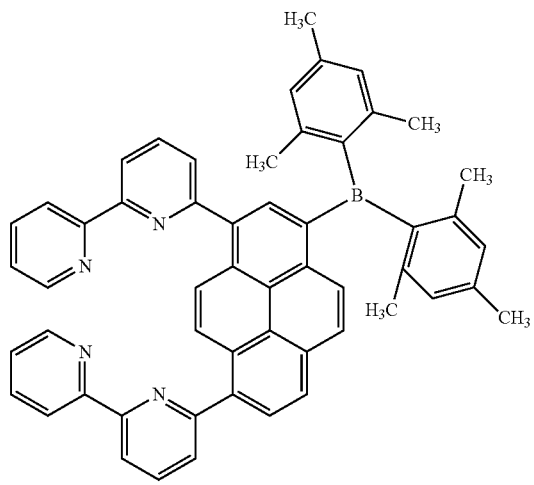
[40]
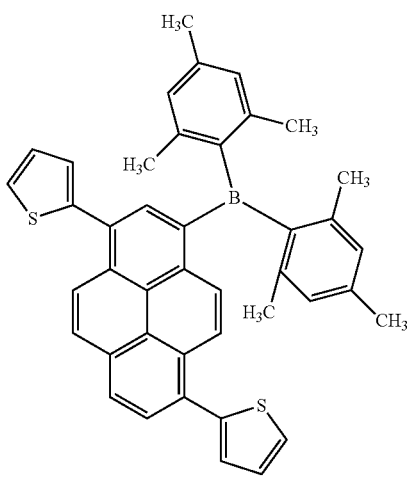

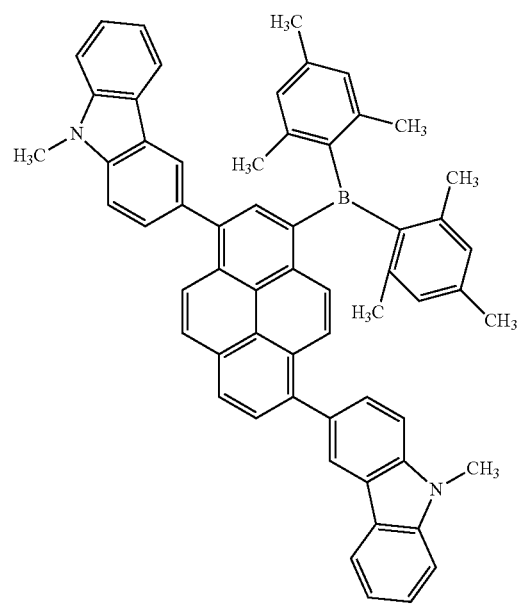
[41]
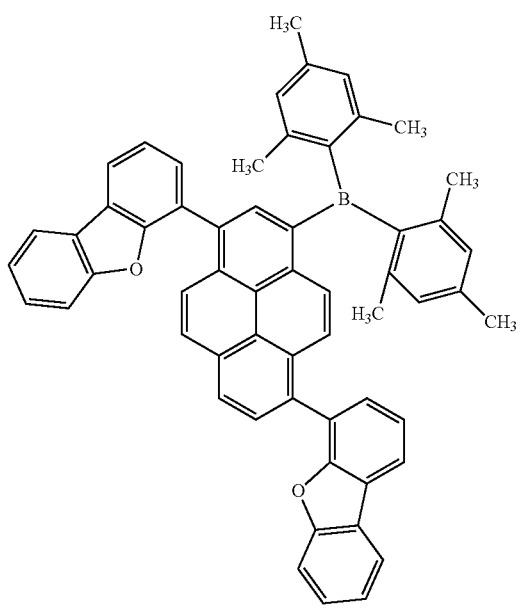
[43]
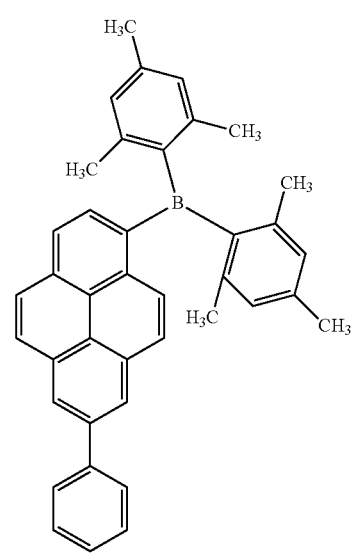
[44]
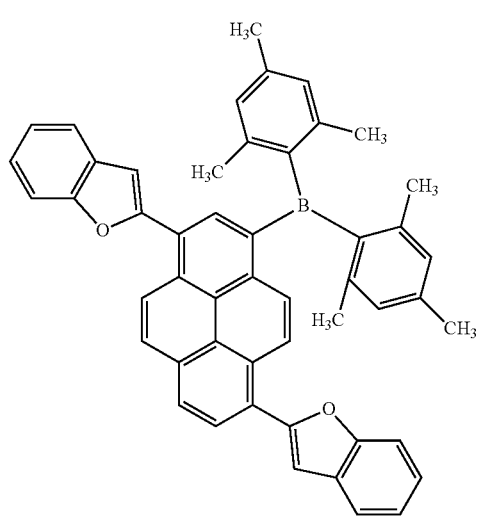
[42]
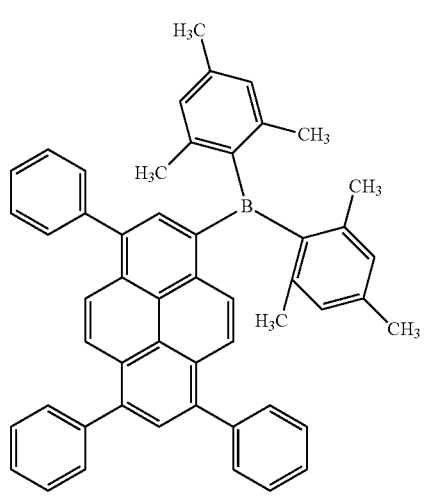
[45]

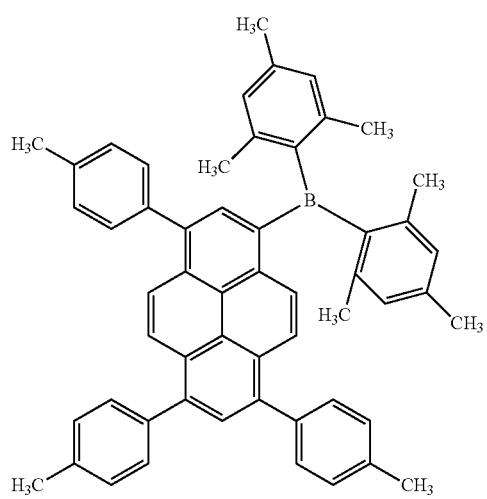
[Chemical Formula 9]
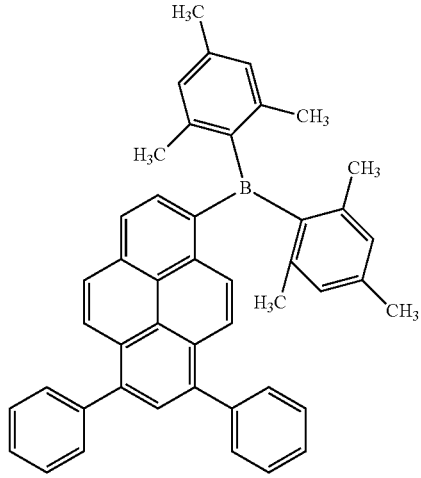
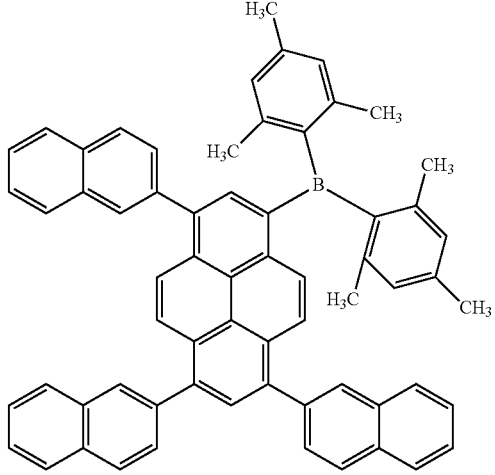

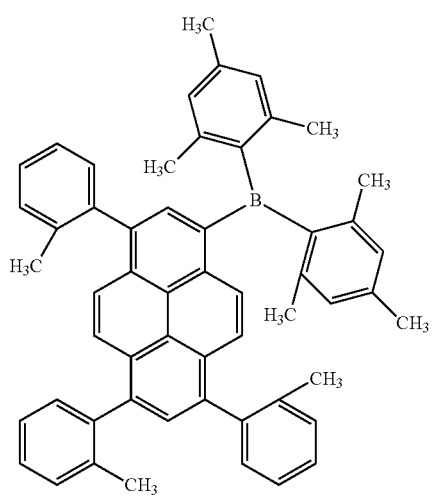
[52]
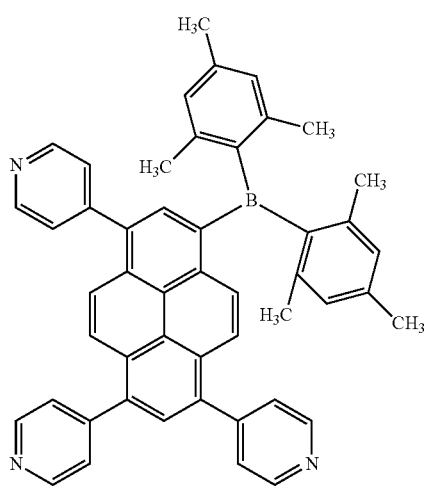
[55]
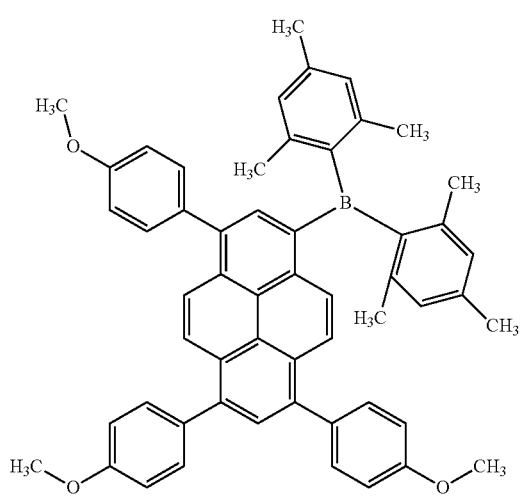
[53]
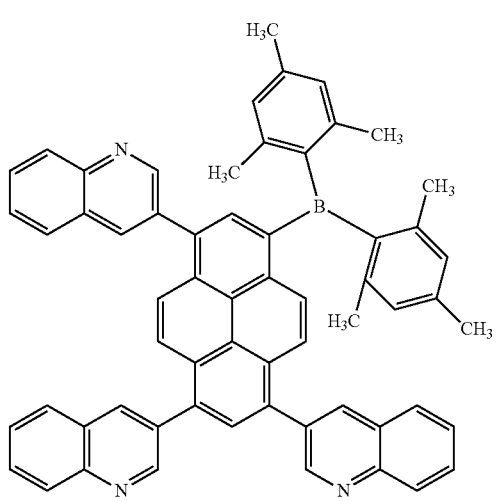
[56]
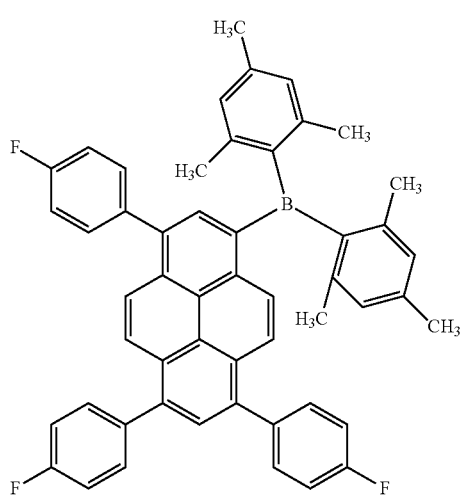
[54]
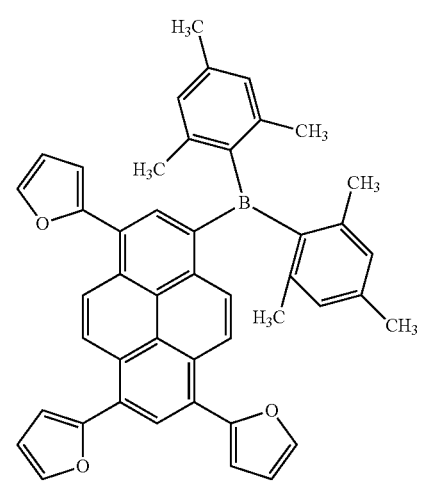
[57]

[58]
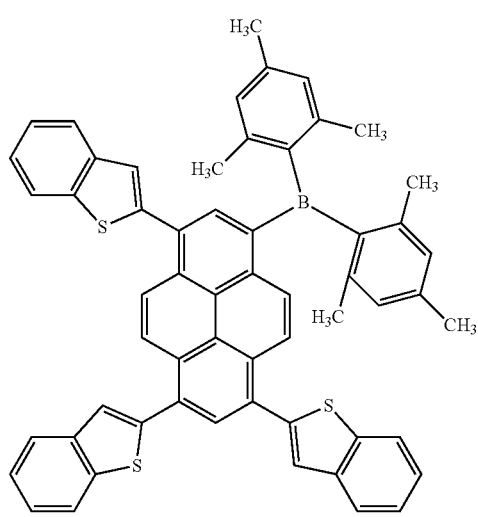
[Chemical Formula 10]
[59]
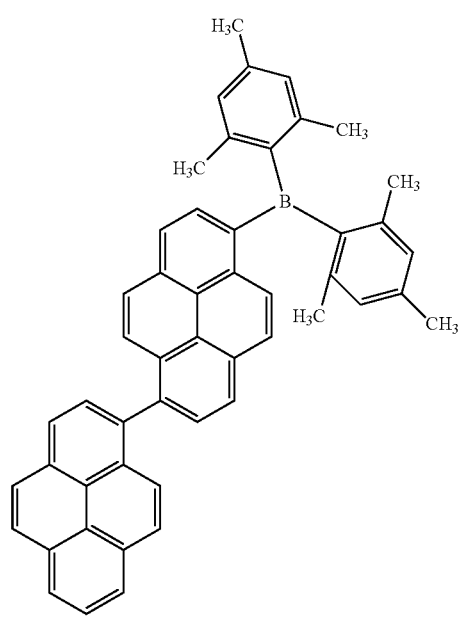
[60]
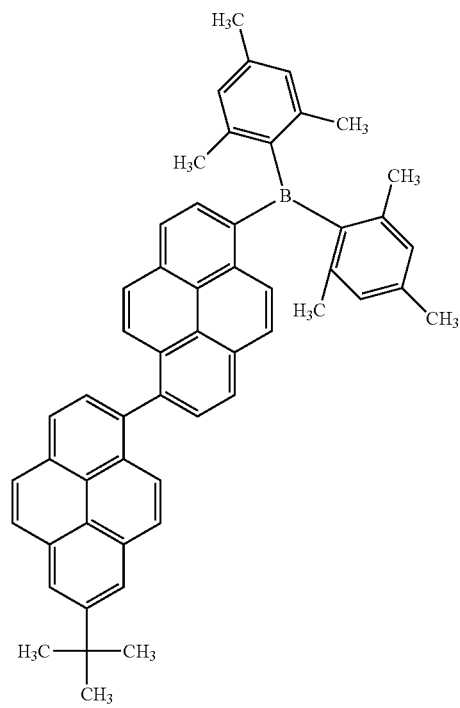
[61]
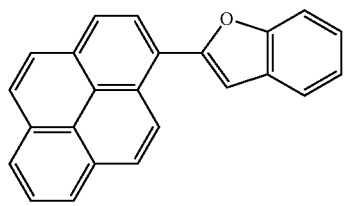
[62]
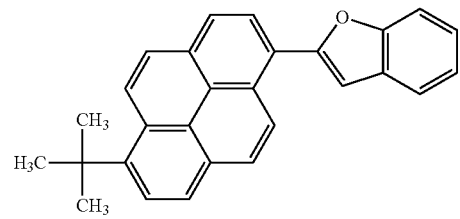
[63]
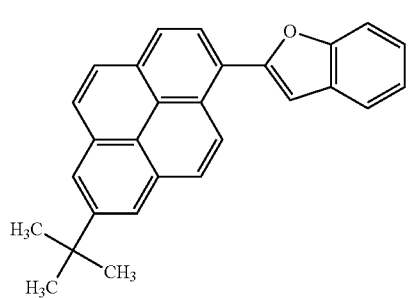

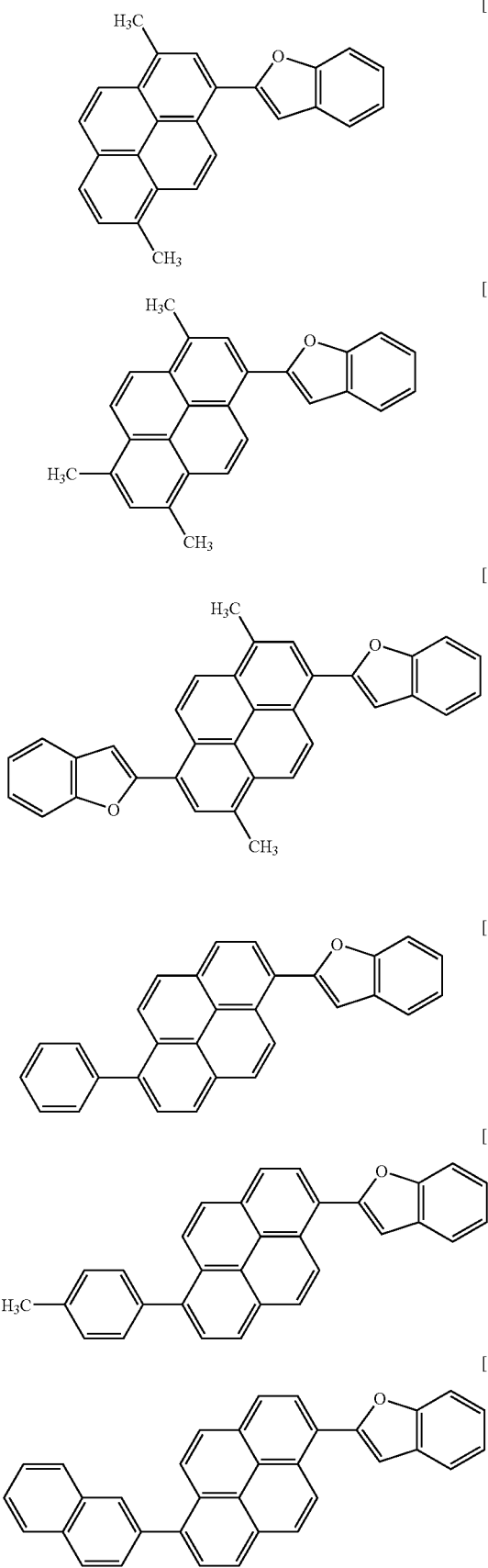
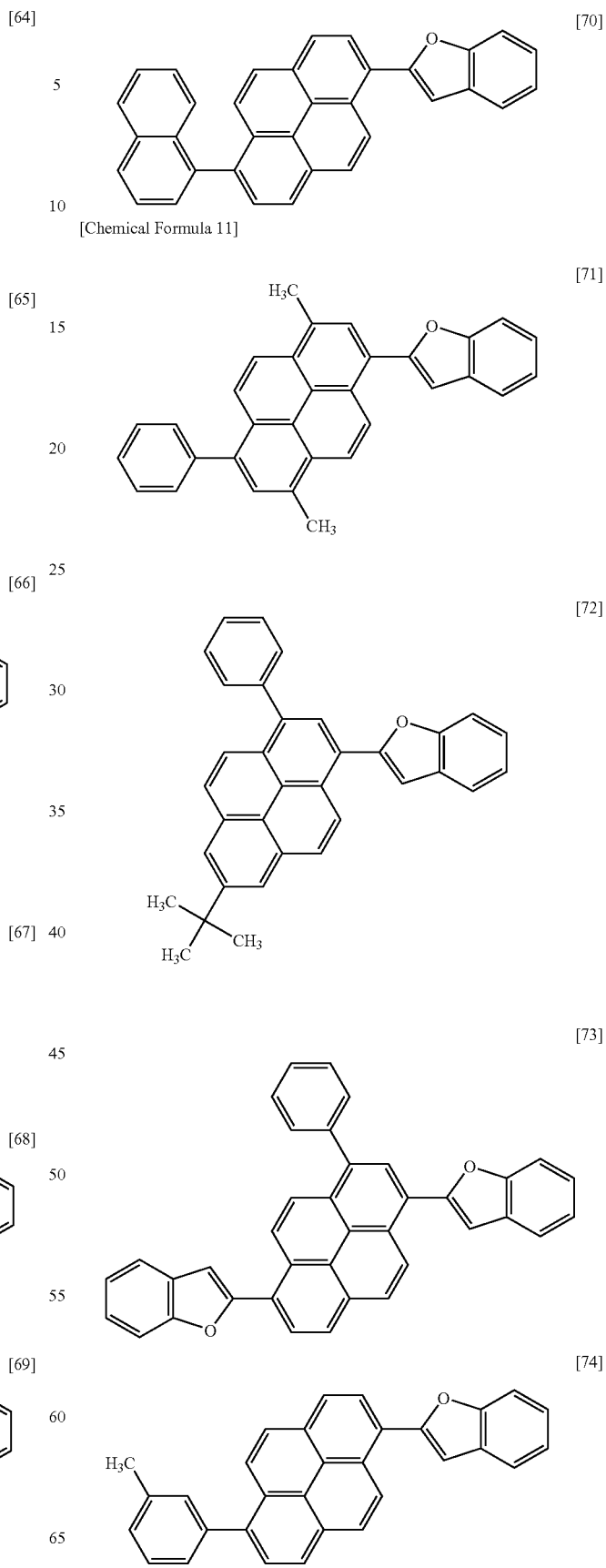

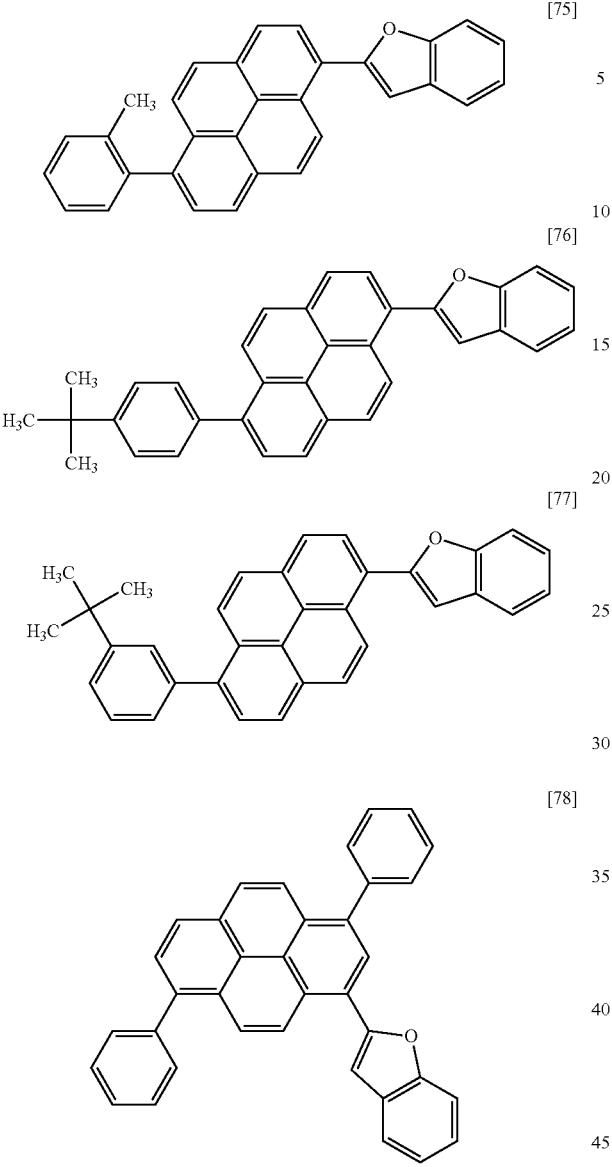
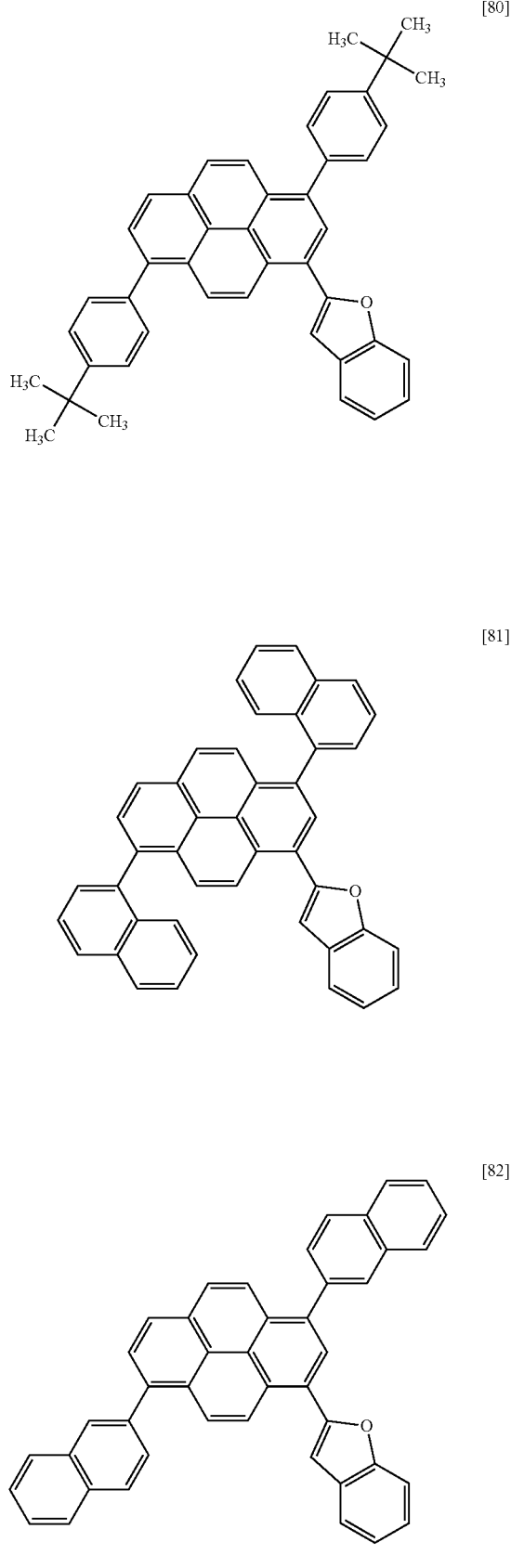

[Chemical Formula 12]
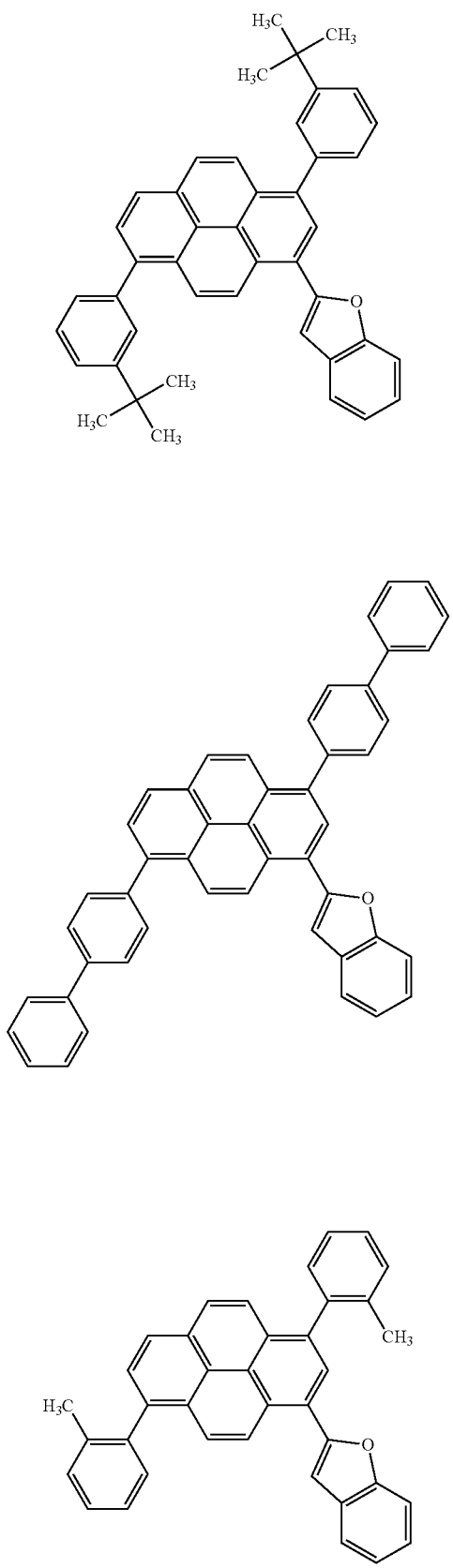
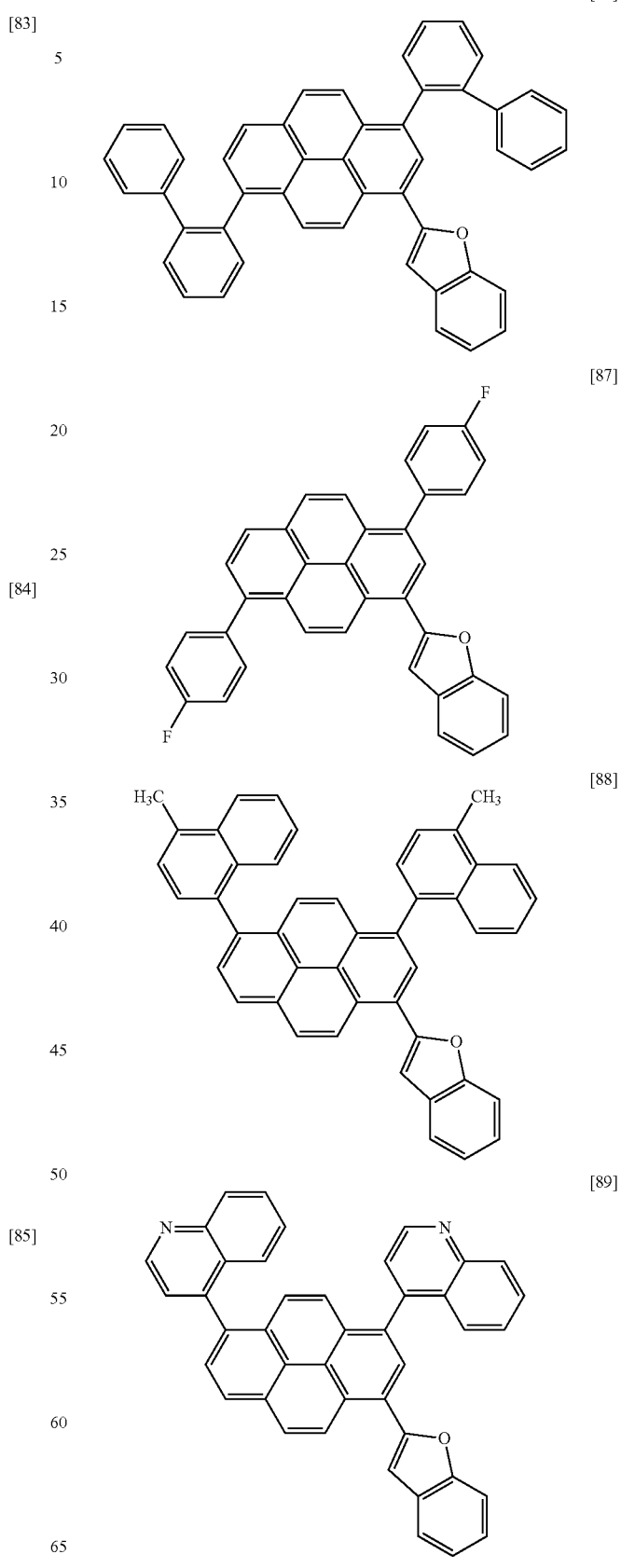

[90] 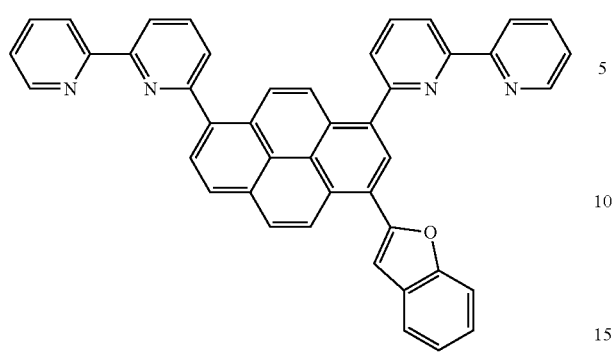
[91] 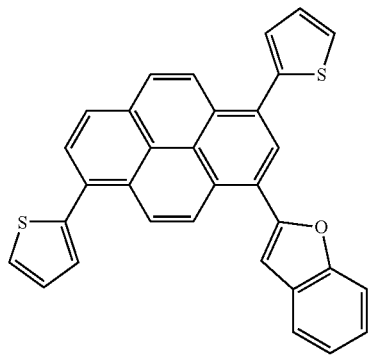
[92] 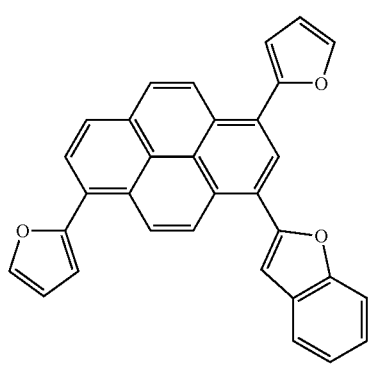
[93] 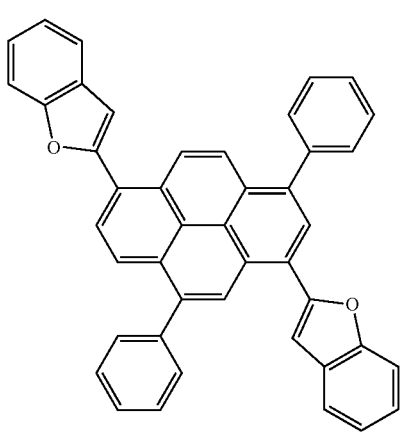
[94] 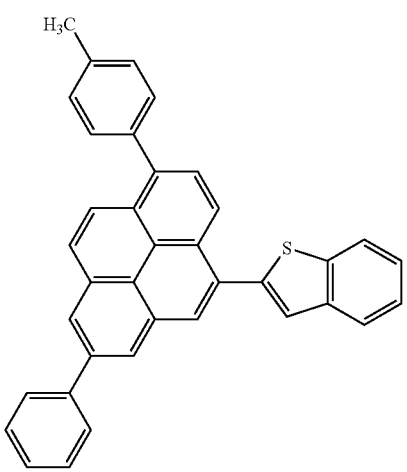
[Chemical Formula 13]
[95] 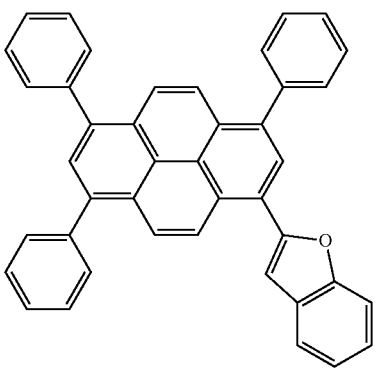
[96] 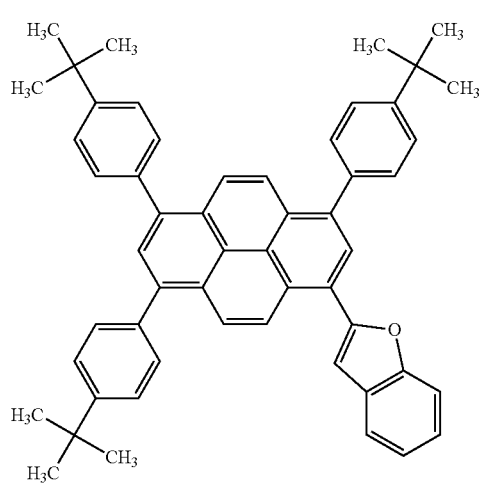

[97]
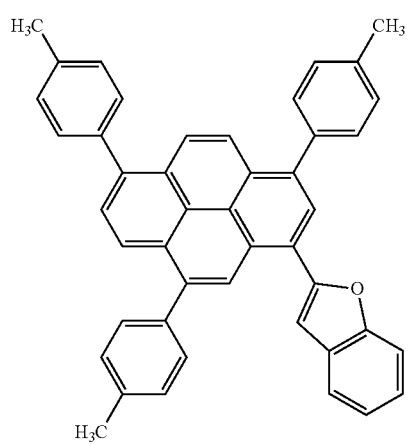
[98]
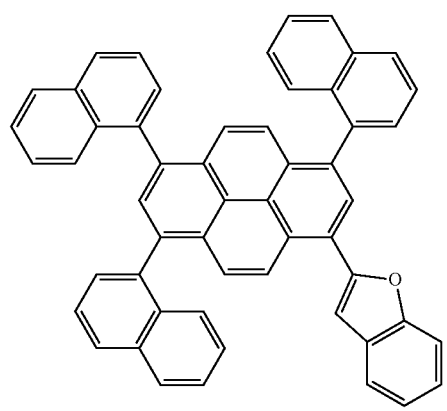
[99]
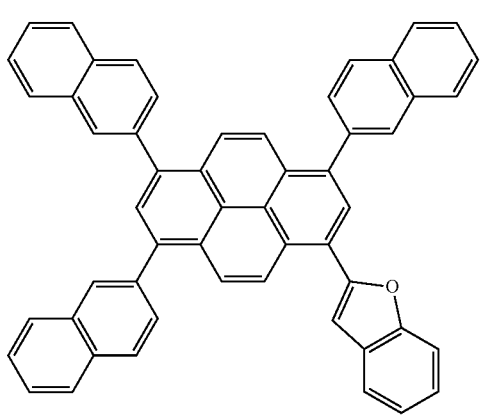
[100]
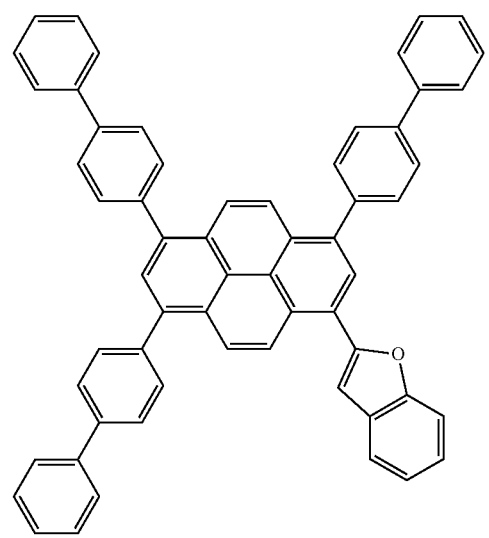
[101]
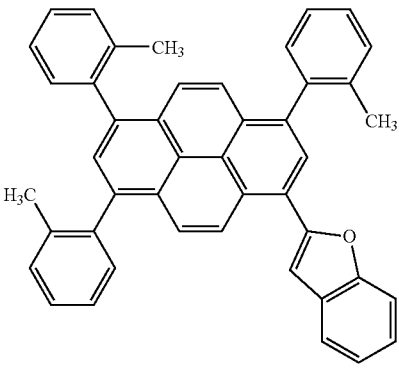
[102]
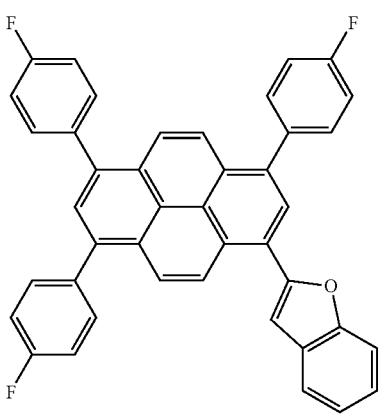

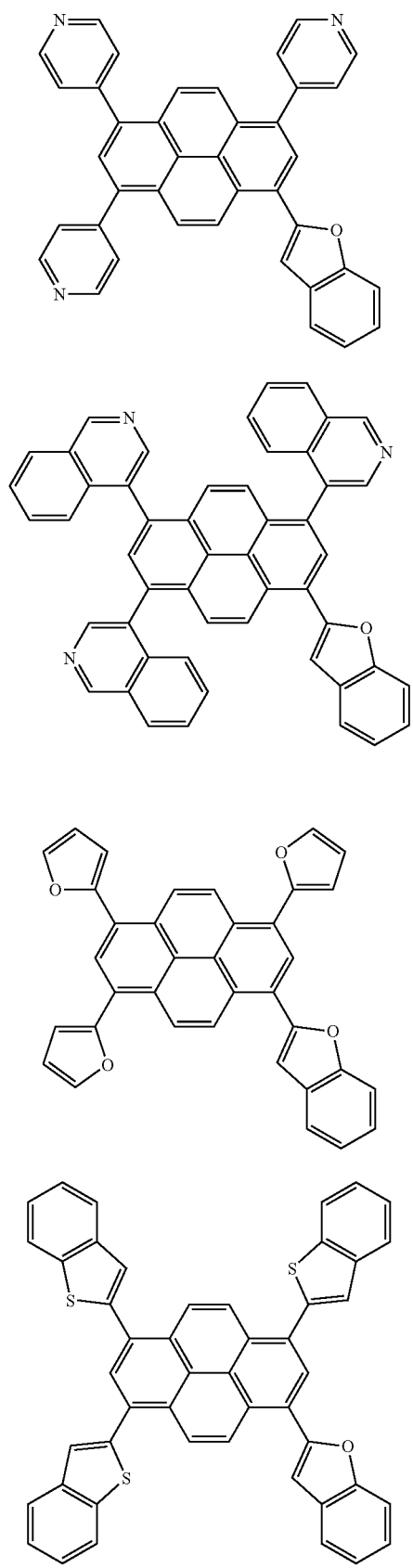
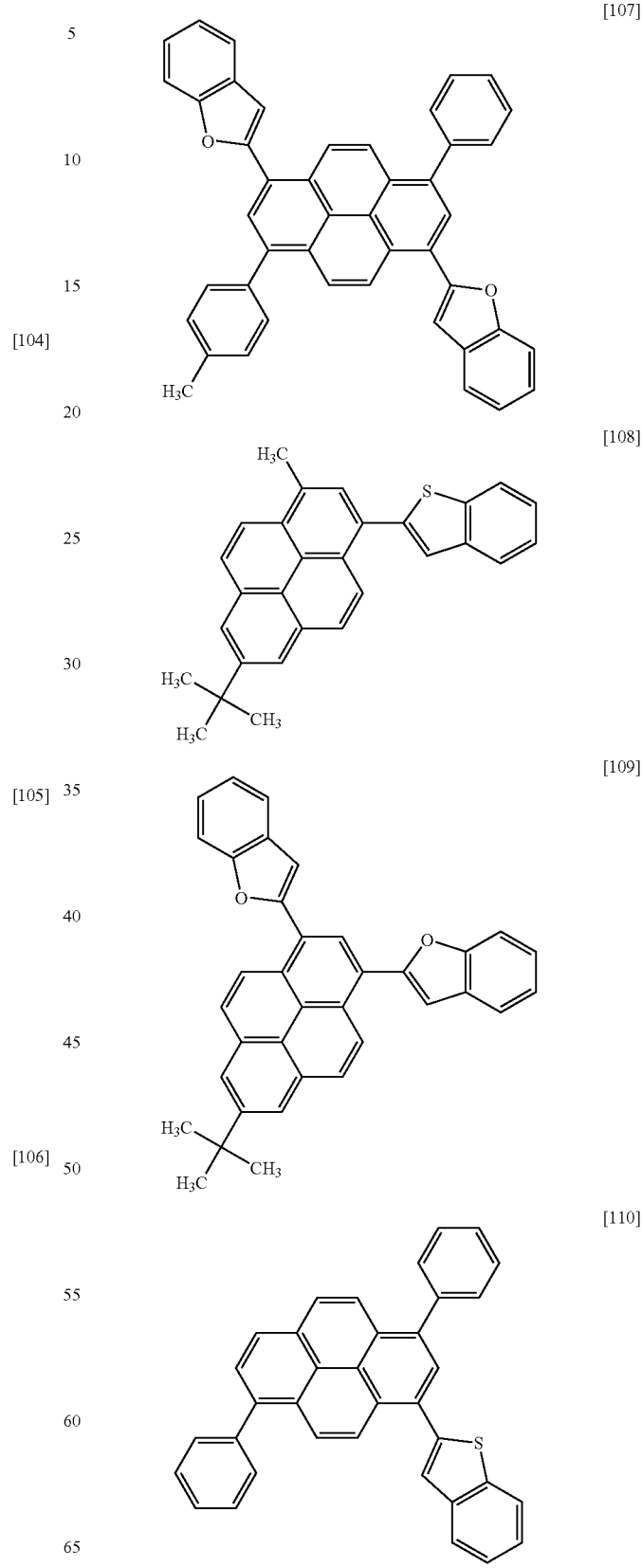
[Chemical Formula 14]

[111] 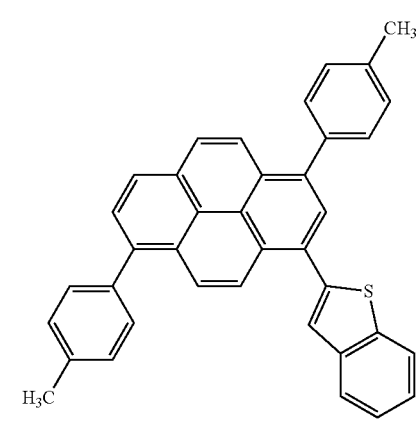
[112] 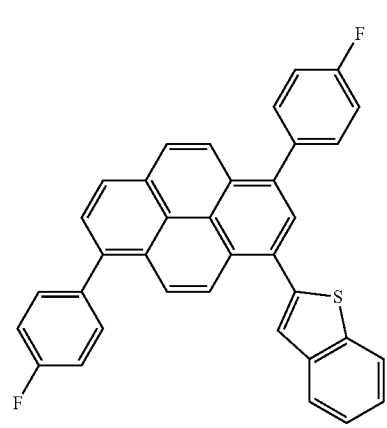
[113] 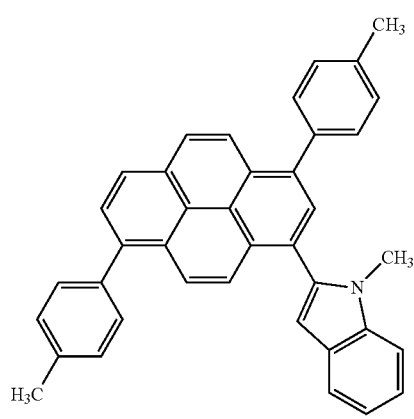
[114] 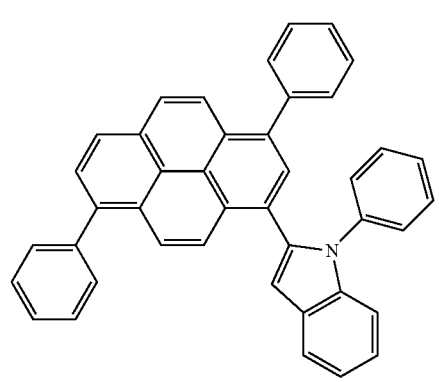
[115] 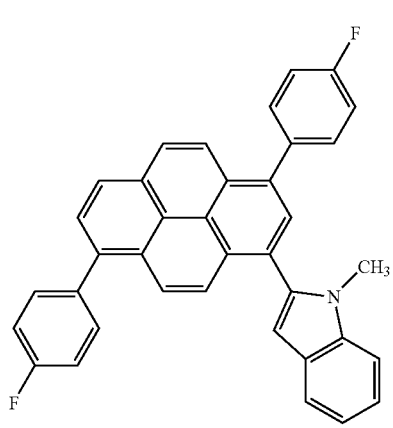
[116] 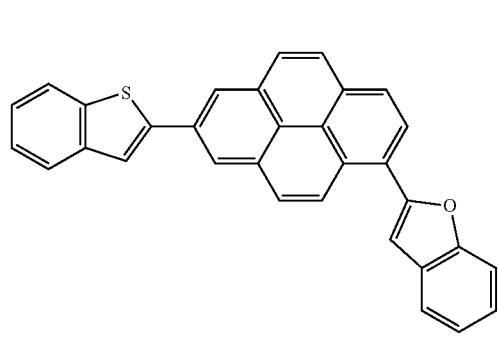
[117] 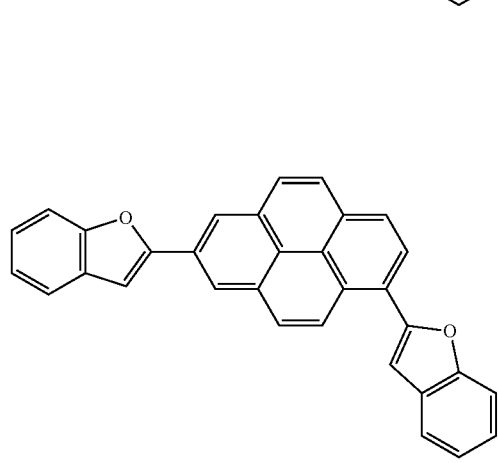
[118] 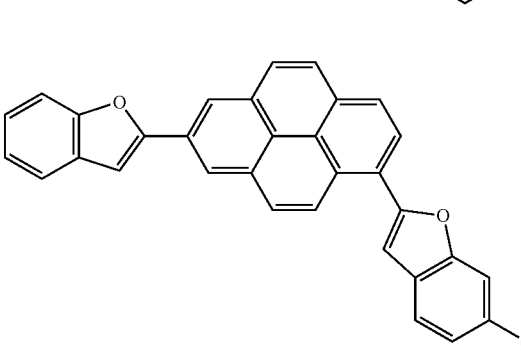

[119]
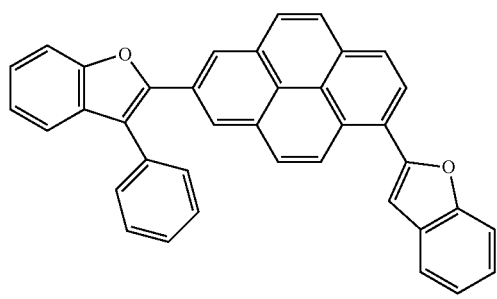
[120]
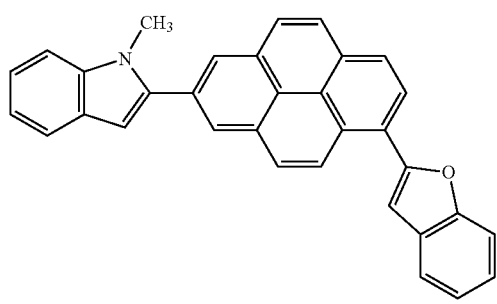
[121]
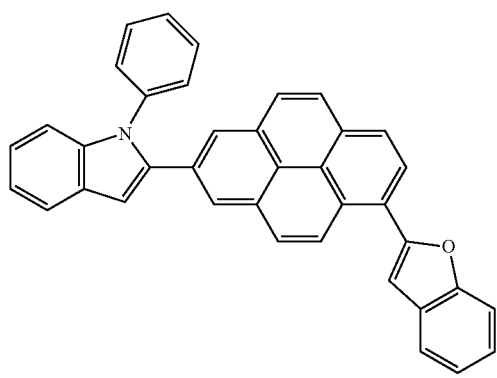
[Chemical Formula 15]
[122]
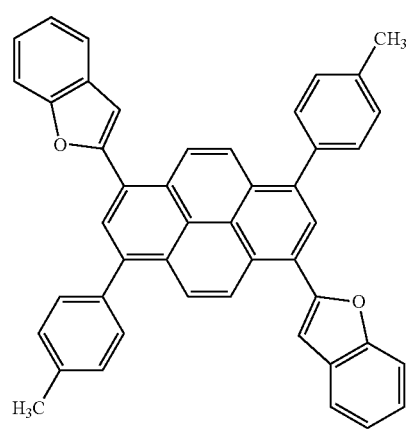
[123]
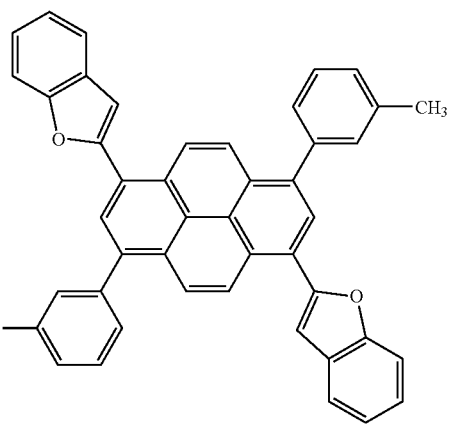
[124]
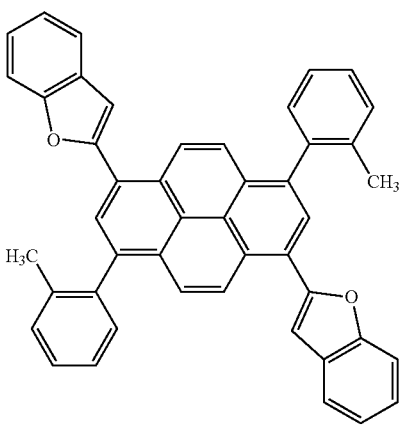
[125]
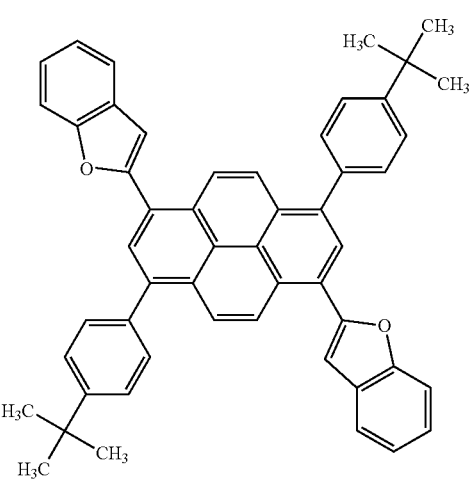

[126]
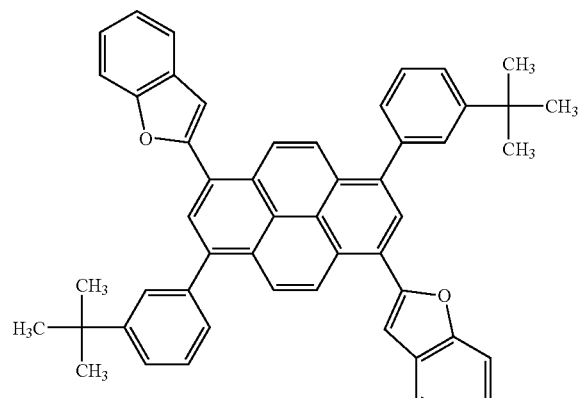
[127]
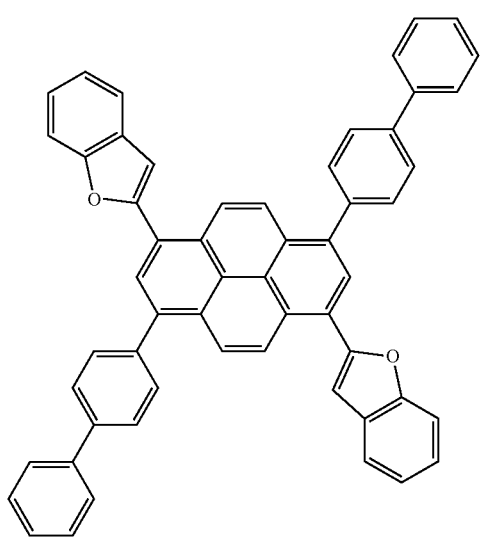
[128]
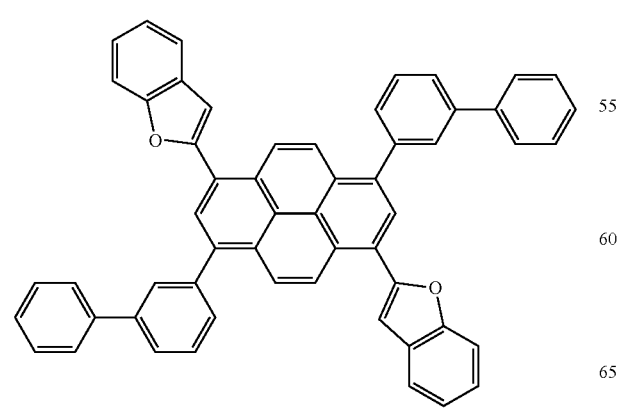
[129]
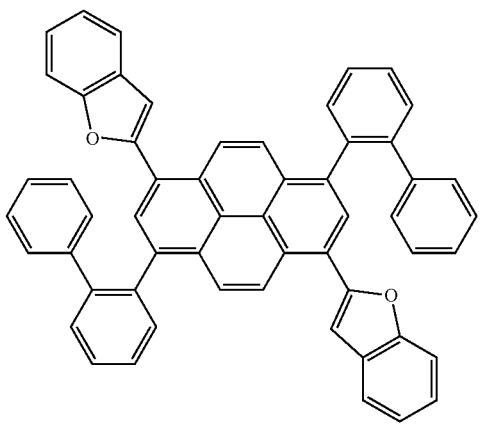
[130]
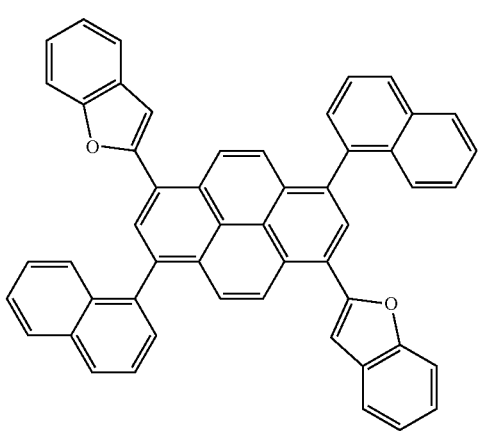
[131]
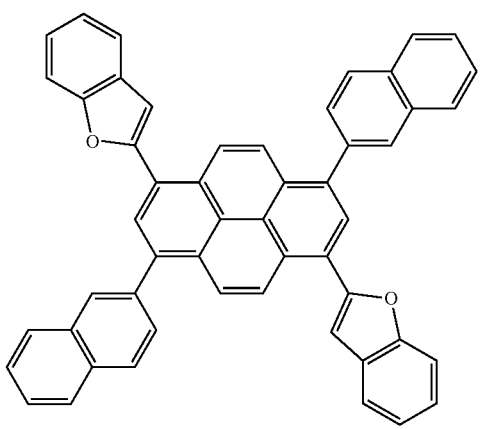

[132]
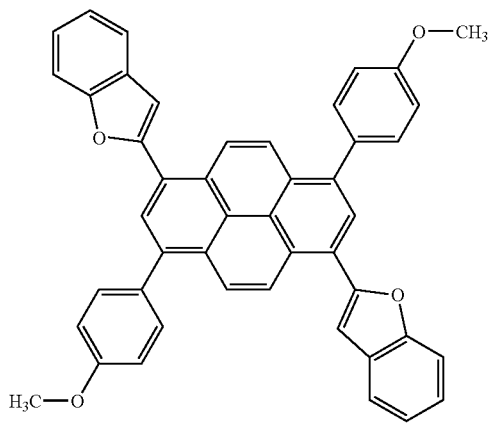
[135]
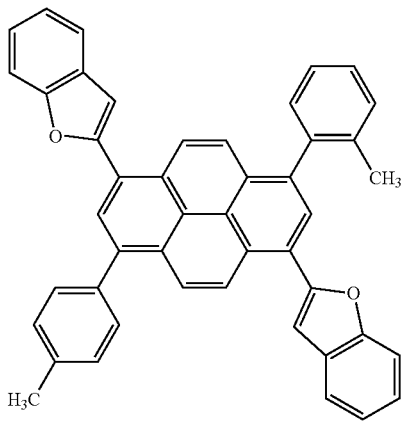
[133]
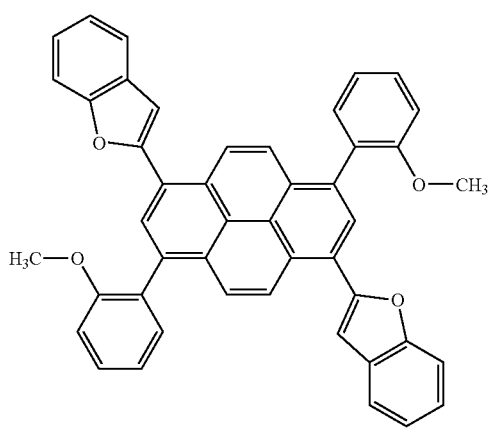
[136]
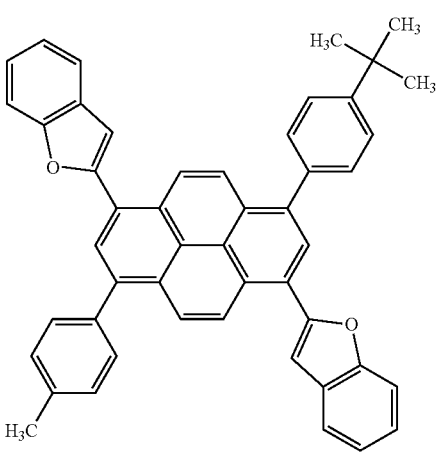
[Chemical Formula 16]
[134]
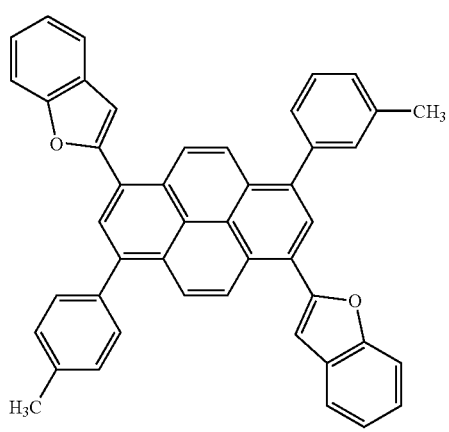
[137]
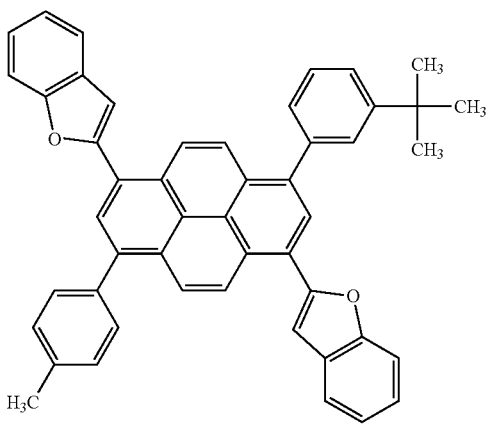

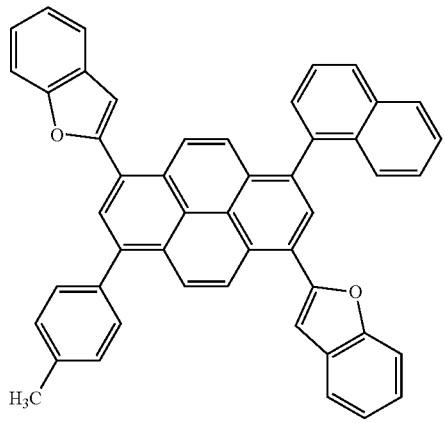
[138]
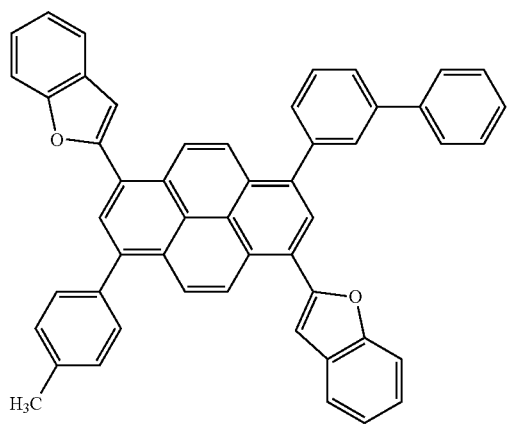
[141]
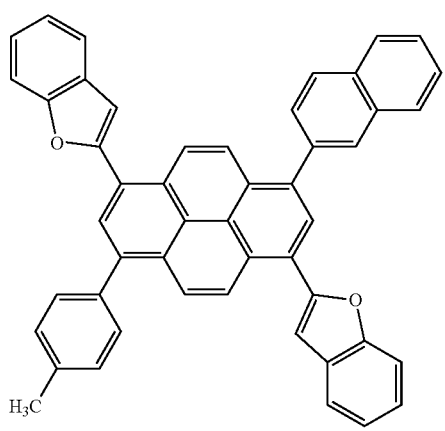
[139]
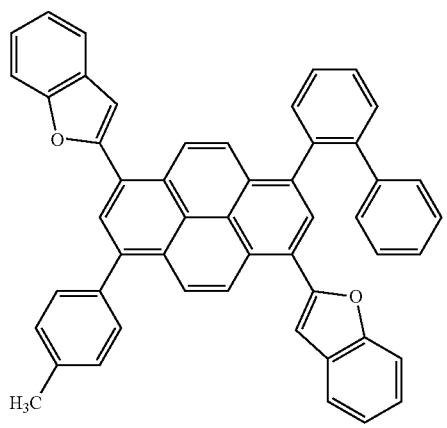
[142]
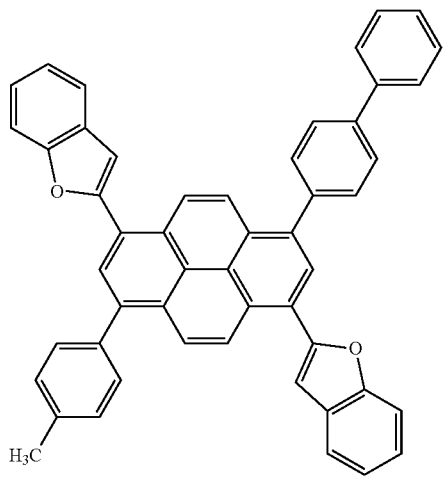
[140]
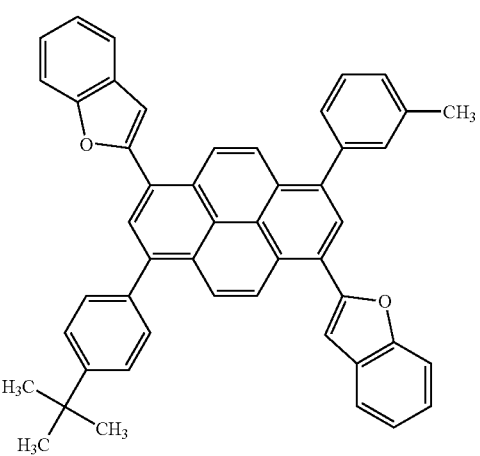
[143]

[144]
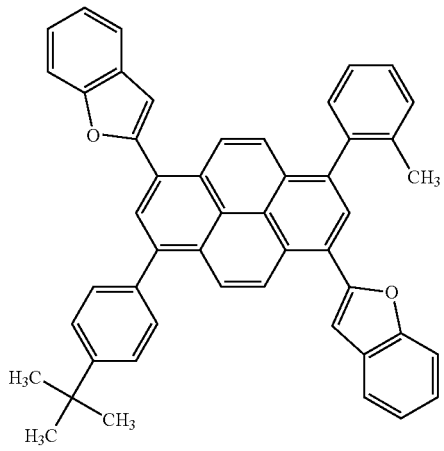
[145]
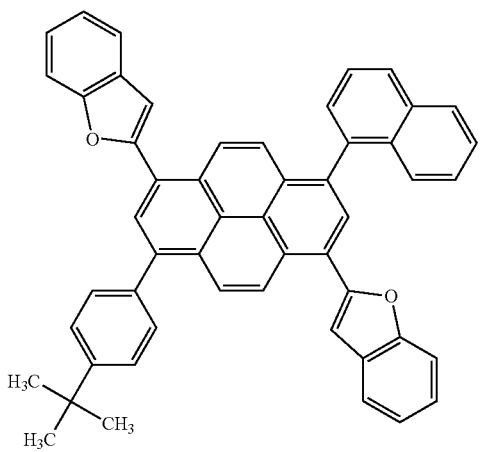
[Chemical Formula 17]
[146]
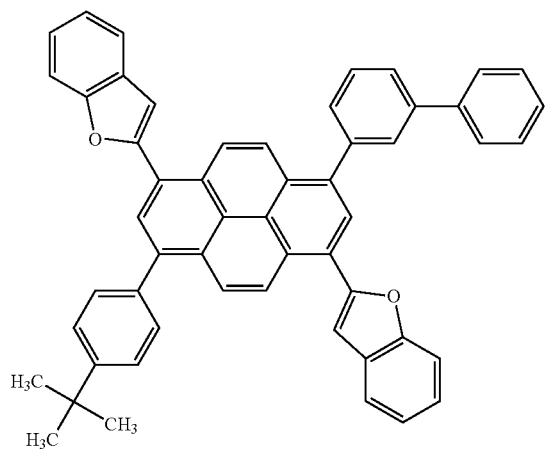
[147]
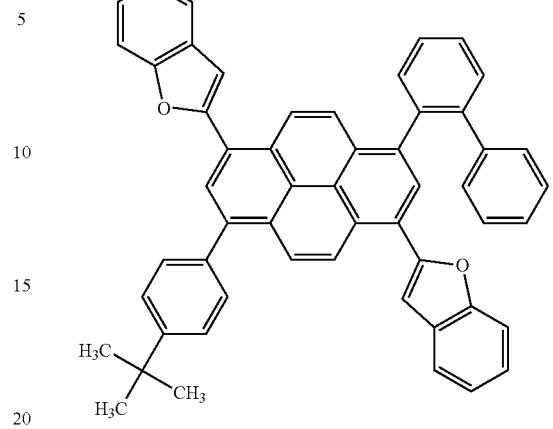
[148]
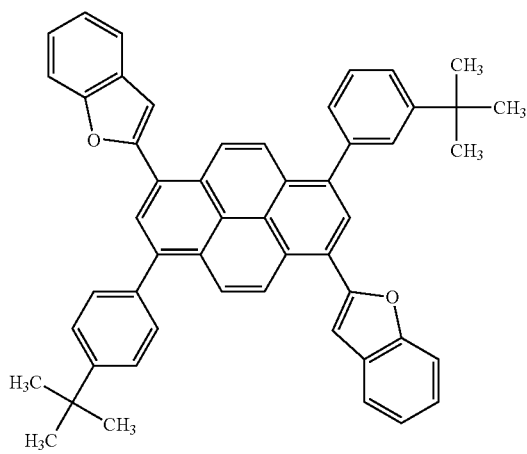
[149]
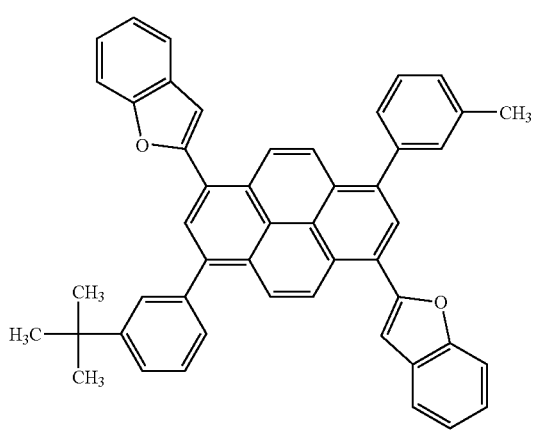

[150]
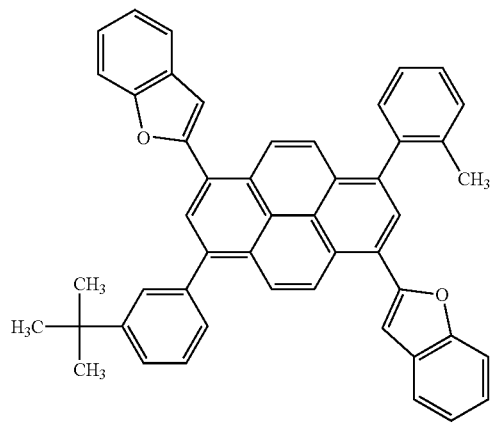
[151]
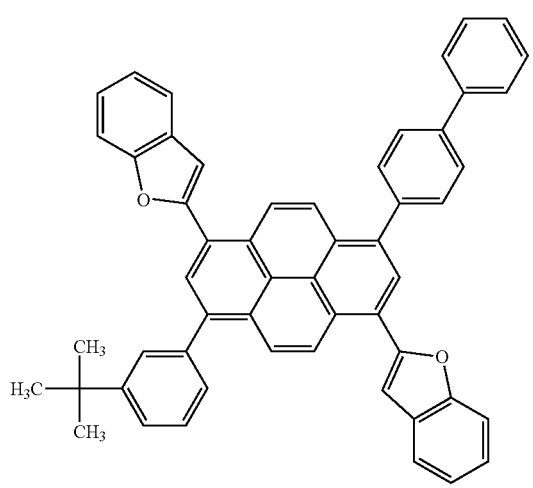
[152]
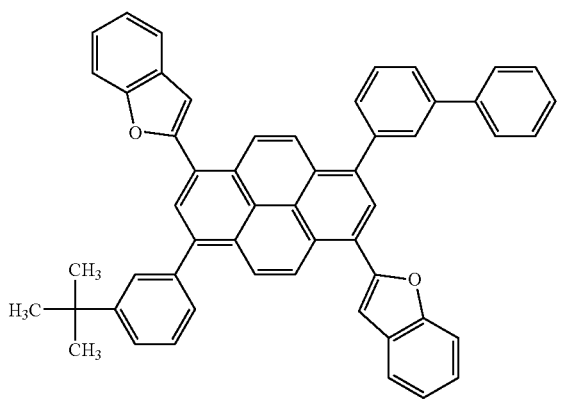
[153]
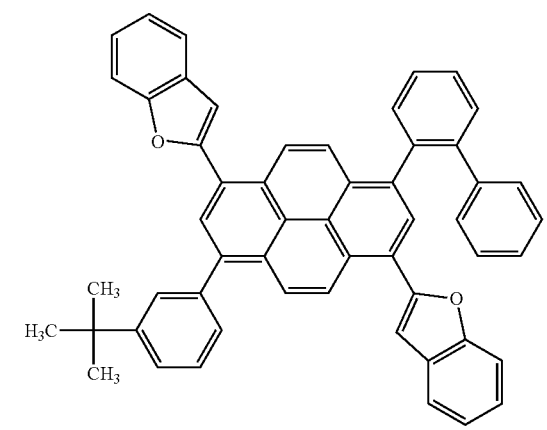
[154]
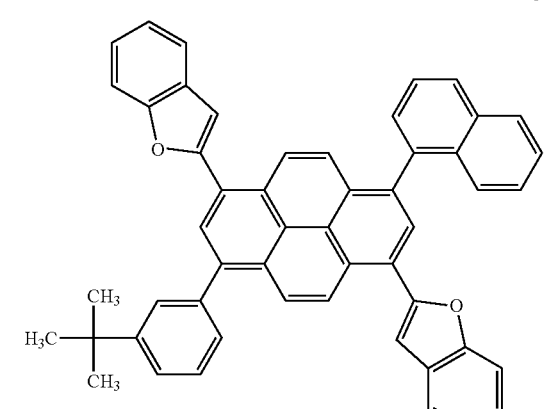
[155]
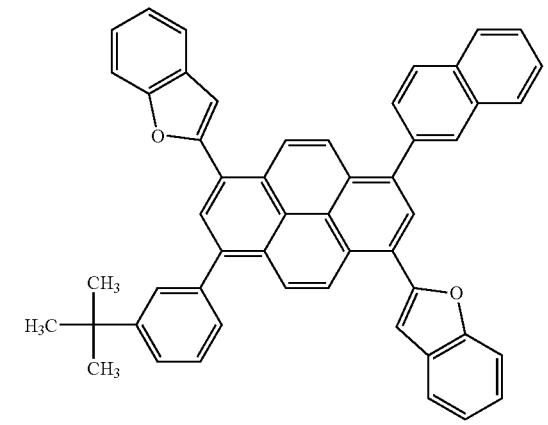

-continued

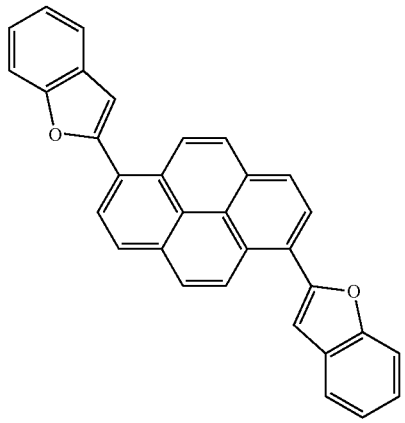

In the synthesis of a pyrene compound represented by the general formula (1), a known method can be used. The method of introducing a diarylboryl group (the general formula (2)) into a pyrene skeletal structure includes, but is not limited to, a method of lithiating a halogenated pyrene using n-butyl lithium and reacting the lithiated pyrene with diaryl fluoride. Examples of the method of introducing a benzofuranyl group, a benzothiophenyl group or an indolyl group (the general formula (3)) into a pyrene skeletal structure include, but are not limited to, a method using a coupling reaction between a halogenated pyrene derivative and a benzofuranyl metal complex or an benzothiophenyl metal complex or an indolyl metal complex in the presence of a palladium or nickel catalyst, and a method using a coupling reaction between a pyrenyl metal complex and a halogenated benzofuran derivative, a halogenated benzothiophene derivative or a halogenated indole derivative in the presence of a palladium or nickel catalyst.

Embodiments of a light emitting device in the present invention will be described in detail below by way of examples and with reference to the drawings. The light emitting device of the present invention comprises an anode, a cathode, and an organic layer existing between the anode and the cathode, and the organic layer includes at least an emissive layer and the emissive layer emits light by means of electric energy.

The organic layer may be composed only of an emissive layer, or has a layer structure of 1) hole transporting layer/emissive layer/electron transporting layer, 2) emissive layer/electron transporting layer or 3) hole transporting layer/emissive layer. Each layer may be composed of a single layer or plural layers. When a hole transporting layer and an electron transporting layer are composed of plural layers, layers contacted with an electrode may be referred to as a hole injection layer and an electron injection layer, respectively. In the following description, the hole injection material is included in the hole transporting material, while the electron injection material is included in the electron transporting material.

FIG. 1 illustrates an embodiment of the light emitting device in which the organic layer is composed only of an emissive layer 005 existing between anode 002 and cathode 007, the anode 002 being provided on a substrate 001.

Figure 2:
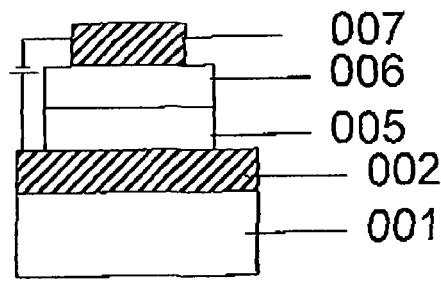
FIG. 2 illustrates a second embodiment of the light emitting device according to the present invention.

FIG. 2 illustrates an embodiment of the light emitting device in which the organic layer is composed of an emissive layer 005 and an electron transporting layer 006 existing between anode 002 and cathode 007, the anode 002 being provided on a substrate 001.

In the light emitting device of the present invention, the light emitting device material of the present invention, which contains a pyrene compound represented by the general formula (1), is contained in the organic layer. Herein, the light emitting device material means a compound relating to light emission in the light emitting device, and corresponds to a material capable of emitting light itself or a material capable of assisting light emission. Specifically, a hole transporting material, an emissive material and an electron transporting material correspond to the light emitting device material.

The light emitting device material of the present invention may be used as a hole transporting material and an electron transporting material, and is preferably used as an emissive material since it has high light emitting performance. The light emitting device material of the present invention is preferably used as a blue emissive material since it emits strong light in a blue region, and can also be used as a material for a green to red light emitting device and a white light emitting device.

The material of the anode is not particularly limited as long as it is a material capable of efficiently injecting holes into the organic layer. It is preferred to use a material having comparatively large work function. Examples of the material of the anode include conductive metal oxides such as tin oxide, indium oxide, zinc indium oxide and indium tin oxide (ITO); metals such as gold, silver and chromium; inorganic conductive substances such as copper iodide and copper sulfide; and conductive polymers such as polythiophene, polypyrrole and polyaniline. These electrode materials may be used alone, or plural materials may be laminated or mixed.

The resistance of the anode is not particularly limited as long as a current required to perform light emission of the light emitting device can be supplied. In view of power consumption of the light emitting device, low resistance is preferred. For example, when the resistance is 300Ω/□ or less, the anode can function as an electrode. Since it becomes possible to supply an ITO substrate having about 10Ω/□, it is particularly preferred to use a product having a low resistance such as 100Ω/□ or less. The thickness of the anode can be optionally selected according to the resistance value, and is usually from 100 to 300 nm.

In order to maintain a mechanical strength of the light emitting device, the anode is preferably formed on a substrate. As the substrate, for example, a glass substrate made of soda glass or non-alkali glass is preferably used. The thickness of the glass substrate may be the thickness enough to maintain the mechanical strength and is therefore 0.5 mm or more. Although non-alkali glass is preferred that small number of ions are eluted from the glass, soda-lime glass with a $SiO_2$ barrier coat is commercially available and can be used. Furthermore, if the anode stably functions, it is not necessary for the substrate to be made of glass and, for example, the anode may be formed on a plastic substrate. The method of forming an anode is not particularly limited and, for example, an electron beam method, a sputtering method and a chemical reaction method can be used.

The material used for a cathode is not particularly limited as long as it is a substance capable of efficiently injecting electrons into the organic layer, and examples thereof include platinum, gold, silver, copper, iron, tin, zinc, aluminum, indium, chromium, lithium, sodium, potassium, cesium, calcium and magnesium, or an alloy thereof. In order to improve element characteristics by increasing electron injection efficiency, for example, lithium, sodium, potassium, cesium, calcium, magnesium or an alloy containing these low work function metals is effective. However, since these low work function metals are often unstable in atmospheric air, a method of doping the organic layer with a trace amount of (1 nm or less in terms of a thickness tester for vacuum deposition) lithium or magnesium to obtain an electrode having high stability is preferably used. An inorganic salt such as lithium fluoride can also be used. In order to protect the electrode, it is preferred to laminate metals such as platinum, gold, silver, copper, iron, tin, aluminum and indium, alloys using these metals, inorganic substances such as silica, titania and silicon nitride, and organic polymer compounds such as polyvinyl alcohol, polyvinyl chloride and a hydrocarbon-based polymer compound. The method of forming a cathode is not particularly limited and, for example, resistance heating, electron beam, sputtering, ion plating and coating can be used.

The hole transporting layer is formed by a method of laminating or mixing one or more kinds of hole transporting materials or a method of using a mixture of a hole transporting material and a polymer binder. A hole transporting layer may be formed by adding an inorganic salt such as iron(III) chloride to a hole transporting material. The hole transporting material is not particularly limited as long as it is a compound which is capable of forming a thin film, injecting holes from the anode and transporting holes. Preferred hole transporting materials are triphenylamine derivatives such as 4,4'-bis(N-(3-methylphenyl)-N-phenylamino)biphenyl, 4,4'-bis(N-(1-naphthyl)-N-phenylamino)biphenyl and 4,4',4"-tris(3-methylphenyl(phenyl)amino)triphenylamine; biscarbazole derivatives such as bis(N-allylcarbazole) and bis(N-alkylcarbazole); heterocyclic compounds such as pyrazoline derivatives, stilbene-based compounds, hydrazone-based compounds, benzofuran derivatives, thiophene derivatives, oxadiazole derivatives, phthalocyanine derivatives and porphyrin derivatives; and polymers such as polycarbonate having the above monomer in the side chain, styrene derivatives, polythiophene, polyaniline, polyfluorene, polyvinylcarbazole and polysilane.

The emissive layer may be made of a mixture of a host material and a dopant material, or a host material alone. Each of the host material and the dopant material may be used alone or in combination. The dopant material may be entirely or partially in the host material. The dopant material may be laminated with the host material or dispersed in the host material. When the amount of the dopant material is too large, concentration quenching occurs. Therefore, the amount of the dopant material is preferably 20% by weight or less, and more preferably 10% by weight or less, based on the total of the host material and the dopant material. Regarding the doping method, the dopant material may be formed by a co-evaporation method with the host material, or evaporation may be performed after preliminarily mixing the host material and the dopant material. The pyrene compound of the present invention may be used as the host material, but is preferably used as the dopant material because of high fluorescence quantum yield.

The ionization potential of the pyrene compound of the present invention is not particularly limited, and is preferably 4.5 eV or more and 7.0 eV or less, and more preferably 5.4 eV or more and 6.4 eV or less. An absolute value of the ionization potential may vary depending on the measuring method. The ionization potential in the present invention is a value measured by an atmospheric air type UV photoelectron analyzer (AC-1, manufactured by RIKENKIKI CO., LTD.) using a thin film formed by evaporated onto an ITO glass substrate in a thickness of 30 nm to 100 nm.

As the dopant material, a pyrene compound represented by the general formula (1) may be used alone, or plural kinds of pyrene compounds may be used in combination. It is possible to use one or more other dopant materials in combination with the pyrene compound represented by the general formula (1). Examples of the mixable dopant material include compound having an aryl ring, such as naphthalene, anthracene, phenanthrene, pyrene, triphenylene, perylene, fluorene and indene, or derivatives thereof (for example, 2-(benzothiazol-2-yl)-9,10-diphenylanthracene, 5,6,11,12-tetraphenylnaphthacene, etc.); compounds having a heteroaryl ring, such as furan, pyrrole, thiophene, silole, 9-silafluorene, 9,9'-spirobisilafluorene, benzothiophene, benzofuran, indole, dibenzothiophene, dibenzofuran, imidazopyridine, phenanthroline, pyrazine, naphthylidine, quinoxaline, pyrrolopyridine and thioxanthene, and derivatives thereof; distyrylbenzene derivatives; aminostyryl derivatives such as 4,4'-bis(2-(4-diphenylaminophenyl)ethenyl)biphenyl and 4,4'-bis(N-(stilbene-4-yl)-N-phenylamino)stilbene; aromatic acetylene derivatives; tetraphenylbutadiene derivatives; stilbene derivatives; aldazine derivatives; pyrromethene derivatives; diketopyrrolo[3,4-c]pyrrole derivatives; cumarin derivatives such as 2,3,5,6-1H,4H-tetrahydro-9-(2'-benzothiazolyl)quinolizino[9,9a,1-gh]cumarin; azole derivatives such as imidazole, thiazole, thiadiazole, carbazole, oxazole, oxadiazole and triazole, and metal complexes thereof; and aromatic amine derivatives such as N,N'-diphenyl-N,N'-di(3-methylphenyl)-4,4'-diphenyl-1,1'-diamine.

Preferred examples of the host material to be contained in the emissive material include, but are not limited to, compounds having a fused aryl ring, such as anthracene and pyrene, and derivatives thereof; aromatic amine derivatives such as N,N'-dinaphthyl-N,N'-diphenyl-4,4'-diphenyl-1,1'-diamine; metal chelated oxynoid compounds such as tris(8-quinolinate)aluminum(III); bisstyryl derivatives such as distyrylbenzene derivatives; tetraphenylbutadiene derivatives; indene derivatives; cumarin derivatives; oxadiazole derivatives; pyrrolopyridine derivatives; perynone derivatives; cyclopentadiene derivatives; oxadiazole derivatives; carbazole derivatives; pyrrlopyrrole derivatives; and polymers such as polyphenylenevinylene derivatives, polyparaphenylene derivatives, polyfluorene derivatives, polyvinylcarbazole derivatives and polythiophene derivatives. It is preferred to use a fused aromatic ring derivative having electron-donating or neutral substituents as a host since superior high luminance efficiency effects of the pyrene compound of the present invention are exerted. Specifically, it is preferred to use a compound selected from anthracene compounds, pyrene compounds and distyrylbenzene derivatives as a host material since higher efficiency is attained when used in combination with the pyrene compound of the present invention.

The electron transporting layer is a layer which transports electrons injected from the cathode. It is required for the electron transporting layer to have high electron injection efficiency and efficiently transport injected electrons. Therefore, the electron transporting layer is preferably composed of a substance which has large electron affinity, large electron mobility and excellent stability and is less likely to generate impurities as a trap during production and use. However, in view of transportation balance between holes and electrons, if the electron transporting layer plays a role of efficiently suppressing flow of holes injected from the anode to the cathode side without being recombined, the effect of improving luminance efficiency is identical to that where the electron transporting layer is composed of a material having high electron transporting ability even if it is composed of a material having not so high electron transporting ability.

Examples of the electron transporting material to be used for the electron transporting layer include, but are not limited to, compounds having a fused aryl ring, such as naphthalene and anthracene, and derivatives thereof; styryl-based aromatic derivatives such as 4,4'-bis(diphenylethenyl)biphenyl; perylene derivatives; perynone derivative; cumarin derivatives; naphthalimide derivatives; quinone derivatives such as anthraquinone and diphenoquinone; phosphorus oxide derivatives; carbazole derivatives; indole derivatives; quinolinol complexes such as tris(8-quinolinolate)aluminum(III); hydroxyazole complexes such as hydroxyphenyloxazole complexes; azomethine complexes; tropolone metal complexes; and flavonol metal complexes. It is preferred that the electron transporting material is made of a compound which is composed of an element selected from among carbon, hydrogen, nitrogen, oxygen, silicon and phosphorus and has a heteroaryl ring structure containing an electron-accepting nitrogen since a driving voltage can be decreased.

The electron-accepting nitrogen means a nitrogen atom which forms a multiple bond between adjacent atoms. Since the nitrogen atom has high electronegativity, the multiple bond has an electron-acceptive property and excellent electron transporting ability, and thus a driving voltage of the light emitting device can be decreased when used for the electron transporting layer. Therefore, a heteroaryl ring containing an electron-accepting nitrogen has high electron affinity. Examples of the heteroaryl ring containing an electron-accepting nitrogen include a pyridine ring, a pyrazine ring, a pyrimidine ring, a quinoline ring, a quinoxaline ring, a naphthylidine ring, a pyrimidopyrimidine ring, a benzoquinoline ring, a phenanthroline ring, an imidazole ring, an oxazole ring, an oxadiazole ring, a triazole ring, a thiazole ring, a thiadiazole ring, a benzooxazole ring, a benzothiazole ring, a benzimidazole ring and a phenanthroimidazole ring.

Examples of preferred compound having a heteroaryl ring structure include benzimidazole derivatives, benzoxazole derivatives, benzthiazole derivatives, oxadiazole derivatives, thiadiazole derivatives, triazole derivatives, pyrazine derivatives, phenanthroline derivatives, quinoxaline derivatives, quinoline derivatives, benzoquinoline derivatives, oligopyridine derivatives such as bipyridine and terpyridine, quinoxaline derivatives and naphthylidine derivatives. Among these compounds, there can be preferably used imidazole derivatives such as tris(N-phenylbenzimidazol-2-yl)benzene; oxadiazole derivatives such as 1,3-bis[(4-tert-butylphenyl)1,3,4-oxadiazolyl]phenylene; triazole derivatives such as N-naphthyl-2,5-diphenyl-1,3,4-triazole; phenanthroline derivatives such as bathocuproine and 1,3-bis(1,10-phenanthrolin-9-yl)benzene; benzoquinoline derivatives such as 2,2'-bis(benzo[h]quinolin-2-yl)-9,9'-spirobifluorene; bipyridine derivatives such as 2,5-bis(6'-(2',2"-bipyridyl))-1,1-dimethyl-3,4-diphenylsilole; terpyridine derivatives such as 1,3-bis(4'-(2,2':6'2"-terpyridinyl))benzene; and naphthylidine derivatives such as bis(1-naphthyl)-4-(1,8-naphthylidin-2-yl)phenylphosphine oxide in view of electron transporting ability. Furthermore, phenanthroline dimmers such as 1,3-bis(1,10-phenanthrolin-9-yl)benzene, 2,7-bis(1,10-phenanthrolin-9-yl)naphthalene and 1,3-bis(2-phenyl-1,10-phenanthrolin-9-yl)benzene; and bipyridine dimmers such as 2,5-bis(6'-(2',2"-bipyridyl))-1,1-dimethyl-3,4-diphenylsilole are particularly preferred since remarkably high effect of improving durability is exerted when used in combination with an emissive layer containing a pyrene compound represented by the general formula (1).

The electron transporting material may be used alone, or two or more kinds of the electron transporting materials may be used in combination, or one or more kinds of other electron transporting materials may be used in combination with the electron transporting material. It is also possible to use in combination with metals such as alkali metals and alkali earth metals. The ionization potential of the electron transporting layer is not particularly limited, and is preferably 5.8 eV or more and 8.0 eV or less, and more preferably 6.0 eV or more and 7.5 eV or less.

Examples of the method of forming each layer constituting the light emitting device include, but are not limited to, a resistance heating evaporation method, an electron beam evaporation method, a sputtering method, a molecular stacking method, a coating method, an ink-jetting method, a printing method and a laser induced thermal transfer method. In view of element characteristics, a resistance heating evaporation method or an electron beam evaporation method is usually preferred.

The thickness of the organic layer varies depending on a resistance value of an emissive substance and cannot be limited, but is selected within a range from 1 to 1,000 nm. Each thickness of the emissive layer, the electron transporting layer and the hole transporting layer is preferably 1 nm or more and 200 nm or less, and more preferably 5 nm or more and 100 nm or less.

The light emitting device of the present invention has a function capable of converting electric energy into light. Reference to electrical energy primarily means direct current but it is also possible to use a pulse current or alternating current. There is no limitation on values of the current and voltage. Taking into account power consumption and the life of the device, the maximum luminance should be obtained at as low energy as possible.

The light emitting device of the present invention is preferably used as matrix and/or segment displays.

Reference to matrix in the present invention means the matrix array of pixels used for display, and by association of pixels the display of characters or images is effected. The shape and size of the pixels is determined by the application. In the case of image and character display by personal computers, monitors and televisions, there are normally used square-shaped pixels with up to 300 μm sides, and in the case of large-size displays such as display panels there are normally used pixels with sides of the mm order. In the case of a monochrome display, there may be arrayed pixels of the same color but, in the case of a color display, red, green and blue pixels are arranged side by side. In such circumstances, typically there are delta and stripe types. The method of driving the matrix may be either the active matrix or passive matrix driving method. Construction is simpler in the case of passive matrix driving, while an active matrix may be superior in operational characteristics, so here too selection will be made according to the application.

Segment type in the present invention means that a pattern is formed so as to display previously-determined data, and there is emission in a predetermined region. Examples include time and temperature displays by digital watches and thermometers, operating-state displays in the case of audio equipment and microwave ovens, vehicle panel displays and the like. Now, the aforesaid matrix and segment displays may also both be present in the same panel.

The light emitting device of the present invention can also be favourably employed as a back light. A back light is primarily used for the purposes of enhancing the visibility of a display means which is not self-illuminating, and it may be employed for liquid crystal display devices, watches, audio equipment, automobile panels, signboards, signs and the like. In particular, liquid crystal display devices and, especially, conventional personal computers, have comprised fluorescent bulbs or light-guiding sheets, so making these thinner has been difficult. However, thin, lightweight, products are possible with backlights employing the light emitting device of the present invention.

EXAMPLES

The present invention will be described below by way of Examples, but the present invention is not limited to the following Examples. Numbers of compounds in the following Examples mean numbers of compounds described in the above chemical formulas. The method for evaluation of structural analysis will be shown below.

$^1$H-NMR was measured by Superconductive FTNMR EX-270 (manufactured by JEOL Ltd.) using a deuterated chloroform solution.

HPLC was measured by a 0.1 g/L chloroform solution using a high performance liquid chromatograph LC-10 (manufactured by Shimadzu Corporation). As an eluent of a column, a mixed solution of an aqueous 0.1% phosphoric acid solution and acetonitrile was used.

Example 1

Synthesis of Compound [1]

1 g of 1-bromopyrene was dissolved in 40 ml of diethylether and 2.3 ml of n-butyl lithium (1.6M hexane solution) was added dropwise under a nitrogen atmosphere at 0° C. After stirring the mixed solution at room temperature for 10 minutes, a solution prepared by dissolving 965 mg of dimesitylboron fluoride in 12 ml of diethylether was added dropwise, followed by heating under reflux for 10 minutes. The solution was cooled to room temperature and then filtered. The resultant solid was recrystallized from ethyl acetate, purified by silica gel chromatography and then vacuum-dried to obtain 0.52 g of a pale yellow crystal. $^1$H-NMR analytical results of the resultant powder as follows and revealed that the pale yellow crystal obtained above is a compound [1].

$^1$H-NMR (CDCl$_3$ (d=ppm)): 1.95(s, 12H), 2.32(s, 6H), 6.81(s, 4H), 7.85-8.19(m, 9H).

This compound [1] was used as a light emitting device material after purification through sublimation under a pressure of 1×10$^{-3}$ Pa at about 180° C. using an oil diffusion pump. HPLC purity (area % at a measuring wavelength of 254 nm) was 99.9% before purification through sublimation and was 99.9% after purification through sublimation.

Example 2

Synthesis of Compound [14]

A mixed solution of 2 g of 1,6-dibromopyrene, 1 g of 4-methylphenylboronic acid, 2.4 g of tripotassium phosphate, 0.4 g of tetrabutylammonium bromide, 22 mg of palladium acetate and 60 ml of dimethylformamide was heated with stirring under a nitrogen gas flow at 130° C. for 6 hours. After cooling the solution to room temperature, 30 ml of water was injected, followed by extraction with 100 ml of dichloromethane. The organic layer was washed twice with 50 ml of water, dried over magnesium sulfate and then evaporated. The resultant concentrate was purified by silica gel column chromatography and then vacuum-dried to obtain 0.7 g of 1-bromo-6-(4-methylphenyl)pyrene.

Next, 634 mg of 1-bromo-6-(4-methylphenyl)pyrene was suspended in 20 ml of diethylether and 1.1 ml of n-butyl lithium (1.6M hexane solution) was added dropwise under a nitrogen atmosphere at 0° C. After stirring the solution at room temperature for 10 minutes, a solution prepared by dissolving 464 mg of dimesitylboron fluoride in 6 ml of diethylether was added dropwise, followed by heating under reflux for 10 minutes. After cooling the solution to room temperature, 10 ml of water was injected, followed by extraction with 30 ml of dichloromethane. The organic layer was washed twice with 10 ml of water, dried over magnesium sulfate and then evaporated. The resultant concentrate was purified by silica gel column chromatography and then vacuum-dried to obtain 0.70 g of a pale yellow crystal. $^1$H-NMR analytical results of the resultant powder as follows and revealed that the pale yellow crystal obtained above is a compound [14].

$^1$H-NMR (CDCl$_3$ (d=ppm)): 1.96(s, 12H), 2.33(s, 6H), 2.50(s, 3H), 6.82(s, 4H), 7.36-7.53(m, 4H), 7.86-8.25(m, 8H).

This compound [14] was used as a light emitting device material after purification through sublimation under a pressure of 1×10$^{-3}$ Pa at about 200° C. using an oil diffusion pump. HPLC purity (area % at a measuring wavelength of 254 nm) was 99.5% before purification through sublimation and was 99.6% after purification through sublimation.

Example 3

Synthesis of Compound [13]

In the same manner as in Example 2, except that phenylboronic acid was used in place of 4-methylphenylboronic acid, synthesis was performed to obtain 0.47 g of a pale yellow crystal. $^1$H-NMR analytical results of the resultant powder as follows and revealed that the pale yellow crystal obtained above is a compound [13].

$^1$H-NMR (CDCl$_3$ (d=ppm)): 1.96(s, 12H), 2.33(s, 6H), 6.82(s, 4H), 7.45-7.63(m, 5H), 7.87-8.22(m, 8H).

This compound [13] was used as a light emitting device material after purification through sublimation under a pressure of 1×10$^{-3}$ Pa at about 200° C. using an oil diffusion pump. HPLC purity (area % at a measuring wavelength of 254 nm) was 99.8% before purification through sublimation and was 99.9% after purification through sublimation.

Example 4

Synthesis of Compound [19]

A mixed solution of 7.0 g of 1-bromopyrene, 4.7 g of 2-naphthaleneboronic acid, 11.6 g of tripotassium phosphate, 1.8 g of tetrabutylammonium bromide, 0.11 g of palladium acetate and 248 ml of dimethylformamide was heated with stirring under a nitrogen gas flow at 130° C. for 5 hours. After cooling the solution to room temperature, 300 ml of water was injected, followed by stirring at room temperature for 0.5 hours. The precipitated solid was collected by filtration and then washed twice with 100 ml of water. The resultant solid was dissolved in 200 ml of dichloromethane, dried over magnesium sulfate, evaporated and then filtered using Celite. The filtrate was evaporated and the residue was washed twice with 100 ml of methanol, and then the precipitated solid was collected by filtration. The solid was vacuum-dried to obtain 7.5 g of 1-(2-naphthyl)pyrene.

Next, a mixed solution of 7.5 g of 1-(2-naphthyl)pyrene, 4.1 g of N-bromosuccinimide and 115 ml of dimethylformamide was heated with stirring under a nitrogen gas flow at 50° C. for 7.5 hours. After cooling the solution to room temperature, 100 ml of water was injected, followed by stirring at room temperature for 0.5 hours. The precipitated solid was collected by filtration, washed twice with 100 ml of water and then washed twice with 100 ml of methanol. The solid was washed three times with 50 ml of 1,2-dimethoxyethane and then vacuum-dried to obtain 2.0 g of 1-bromo-6-(2-naphthyl) pyrene.

Next, 1.0 g of 1-bromo-6-(2-naphthyl)pyrene was suspended in 25 ml of diethylether and 1.7 ml of n-butyl lithium (1.6M hexane solution) was added dropwise under a nitrogen atmosphere at 0° C. After stirring the solution at room temperature for 10 minutes, a solution prepared by dissolving 746 mg of dimesitylboron fluoride in 8 ml of diethylether was added dropwise, followed by heating under reflux for 10 minutes. After cooling the solution to room temperature, 10 ml of water was injected, followed by extraction with 30 ml of dichloromethane. The organic layer was washed twice with 10 ml of water, dried over magnesium sulfate and then evaporated. The resultant concentrate was purified by silica gel column chromatography and then vacuum-dried to obtain 0.63 g of a pale yellow crystal 0.63 g. $^1$H-NMR analytical results of the resultant powder as follows and revealed that the pale yellow crystal obtained above is a compound [19].

$^1$H-NMR (CDCl$_3$ (d=ppm)): 1.96(s, 12H), 2.33(s, 6H), 6.82(s, 4H), 7.54-7.60(m, 2H), 7.74-7.78(m, 1H), 7.89-8.26 (m, 12H).

This compound [19] was used as a light emitting device material after purification through sublimation under a pressure of 1×10$^{-3}$ Pa at about 210° C. using an oil diffusion pump. HPLC purity (area % at a measuring wavelength of 254 nm) was 99.6% before purification through sublimation and was 99.9% after purification through sublimation.

Example 5

Synthesis of Compound [61]

A mixed solution of 1.1 g of 1-bromopyrene, 0.8 g of 2-benzofuranboronic acid, 2.1 g of tripotassium phosphate, 98 mg of PdCl$_2$(dppf).CH$_2$Cl$_2$ and 15 ml of deaerated dimethylformamide was heated with stirring under a nitrogen gas flow at 130° C. for 3 hours. After cooling solution to room temperature, 30 ml of water was injected, followed by extraction with 50 ml of dichloromethane. The organic layer was washed twice with 50 ml of water, dried over magnesium sulfate and then evaporated. The resultant concentrate was purified by silica gel column chromatography and then vacuum-dried to obtain 0.34 g of a yellow crystal. $^1$H-NMR analytical results of the resultant powder as follows and revealed that the yellow crystal obtained above is a compound [61].

$^1$H-NMR (CDCl$_3$ (d=ppm)): 7.25-7.41(m, 3H), 7.65-7.74 (m, 2H), 8.02-8.27(m, 7H), 8.40-8.43(m, 1H), 8.80(d, 1H).

This compound [61] was used as a light emitting device material after purification through sublimation under a pressure of 1×10$^{-3}$ Pa at about 180° C. using an oil diffusion pump. HPLC purity (area % at a measuring wavelength of 254 nm) was 99.0% before purification through sublimation and was 99.4% after purification through sublimation.

Example 6

Synthesis of Compound [156]

A mixed solution of 0.72 g of 1,6-dibromopyrene, 0.8 g of 2-benzofuranboronic acid, 2.1 g of tripotassium phosphate, 98 mg of PdCl$_2$(dppf).CH$_2$Cl$_2$ and 15 ml of deaerated dimethylformamide was heated with stirring under a nitrogen gas flow at 130° C. for 4 hours. After cooling the solution to room temperature, 30 ml of water was injected, followed by filtration. The resultant solid was washed with 30 ml of ethanol, recrystallized from dimethylformamide and then vacuum-dried to obtain 0.51 g of a yellow crystal. $^1$H-NMR analytical results of the resultant powder as follows and revealed that the yellow crystal obtained above is a compound [156].

$^1$H-NMR (CDCl$_3$ (d=ppm)): 7.26-7.42(m, 6H), 7.66-7.75 (m, 4H), 8.18-8.30(m, 4H), 8.42-8.45(m, 2H), 8.84(d, 2H).

This compound [156] was used as a light emitting device material after purification through sublimation under a pressure of 1×10$^{-3}$ Pa at about 220° C. using an oil diffusion pump. HPLC purity (area % at a measuring wavelength of 254 nm) was 99.2% before purification through sublimation and was 99.3% after purification through sublimation.

Example 7

Synthesis of Compound [79]

A mixed solution of 2 g of 1,6-dibromopyrene, 1.9 g of 4-methylphenylboronic acid, 5.9 g of tripotassium phosphate, 0.9 g of tetrabutylammonium bromide, 15 mg of palladium acetate and 30 ml of dimethylformamide was heated with stirring under a nitrogen gas flow at 130° C. for 6 hours. After cooling the solution to room temperature, 30 ml of water was injected, followed by filtration. The resultant solid was washed with 30 ml of ethanol, recrystallized from toluene and then vacuum-dried to obtain 1.3 g of 1,6-bis(4-methylphenyl)pyrene.

Next, a mixed solution of 1.3 g of 1,6-bis(4-methylphenyl) pyrene, 0.6 g of N-bromosuccinimide and 30 ml of dimethylformamide was stirred under a nitrogen gas flow at 60° C. for 5 hours. After cooling the solution to room temperature, 30 ml of water was injected, followed by extraction with 100 ml of dichloromethane. The organic layer was washed twice with 50 ml of water, dried over magnesium sulfate and then evaporated. The resultant solid was recrystallized from toluene and then vacuum-dried to obtain 1.0 g of 3-bromo-1,6-bis(4-methylphenyl)pyrene.

Next, a mixed solution of 1.0 g of 3-bromo-1,6-bis(4-methylphenyl)pyrene, 1.6 g of 2-(4,4,5,5-tetramethyl-1,3,2-dioxaborolan-2-yl)benzo[b]furan, 2.8 g of tripotassium phosphate, 57 mg of PdCl$_2$(dppf).CH$_2$Cl$_2$ and 25 ml of deaerated dimethylformamide was heated with stirring under a nitrogen gas flow at 100° C. for 4 hours. After cooling the solution to a room temperature, 30 ml of water was injected, followed by filtration. The resultant solid was washed with 30 ml of methanol, purified by silica gel column chromatography and then vacuum-dried to obtain 0.34 g of a yellow crystal. $^1$H-NMR analytical results of the resultant powder as follows and revealed that the yellow crystal obtained above is a compound [79].

$^1$H-NMR (CDCl$_3$ (d=ppm)): 2.51(ss, 6H), 7.24-7.42(m, 7H), 7.55-7.70(m, 6H), 7.99-8.40(m, 6H), 8.74(d, 1H).

This compound [79] was used as a light emitting device material after purification through sublimation under a pressure of 1×10$^{-3}$ Pa at about 220° C. using an oil diffusion pump. HPLC purity (area % at a measuring wavelength of 254 nm) was 99.4% before purification through sublimation and was 99.5% after purification through sublimation.

Example 8

Synthesis of Compound [87]

A mixed solution of 2 g of 1,6-dibromopyrene, 2.3 g of 4-fluorophenylboronic acid, 7.0 g of tripotassium phosphate, 1.1 g of tetrabutylammonium bromide, 74 mg of palladium acetate and 50 ml of dimethylformamide was heated with stirring under a nitrogen gas flow at 130° C. for 6 hours. After cooling the solution to room temperature, 50 ml of water was injected, followed by extraction with 100 ml of dichloromethane. The organic layer was washed twice with 50 ml of water, dried over magnesium sulfate and then evaporated. The resultant solid was washed with 30 ml of methanol and then vacuum-dried to obtain 1.8 g of 1,6-bis(4-fluorophenyl) pyrene.

Next, a mixed solution of 1.8 g of 1,6-bis(4-fluorophenyl) pyrene, 835 mg of N-bromosuccinimide and 60 ml of dimethylformamide was stirred under a nitrogen gas flow at 80° C. for 5 hours. After cooling the solution to room temperature, the resultant precipitate was filtered. The solid was washed with 30 ml of methanol and then vacuum-dried to obtain 951 mg of 3-bromo-1,6-bis(4-fluorophenyl)pyrene.

Next, a mixed solution of 951 mg of 3-bromo-1,6-bis(4-fluorophenyl)pyrene, 1.6 g of 2-(4,4,5,5-tetramethyl-1,3,2-dioxaborolan-2-yl)benzo[b]furan, 2.8 g of tripotassium phosphate, 57 mg of $PdCl_2(dppf).CH_2Cl_2$ and 25 ml of deaerated dimethylformamide was heated with stirring under a nitrogen gas flow at 100° C. for 4 hours. After cooling to room temperature, 30 ml of water was injected, followed by filtration. The resultant solid was washed with 30 ml of methanol, purified by silica gel column chromatography and then recrystallized from toluene. After vacuum drying, 0.22 g of a yellow crystal was obtained. $^1$H-NMR analytical results of the resultant powder as follows and revealed that the yellow crystal obtained above is a compound [87].

$^1$H-NMR ($CDCl_3$ (d=ppm)): 7.24-7.39(m, 7H), 7.58-7.71 (m, 6H), 7.98-8.38(m, 6H), 8.77(d, 1H).

This compound [87] was used as a light emitting device material after purification through sublimation under a pressure of $1\times10^{-3}$ Pa at about 210° C. using an oil diffusion pump. HPLC purity (area % at a measuring wavelength of 254 nm) was 99.3% before purification through sublimation and was 99.4% after purification through sublimation.

Example 9

Synthesis of Compound [97]

A mixed solution of 5 g of 1-bromopyrene 5 g, 7.9 g of N-bromosuccinimide and 140 ml of dimethylformamide was stirred under a nitrogen gas flow at 80° C. for 10 hours. After cooling to room temperature, 400 ml of water was injected and the precipitate was filtered. The solid separated by filtration was washed in turn with 50 ml of water, 100 ml of methanol and 200 ml of dichloromethane and then vacuum-dried to obtain 6.1 g of 1,3,6-tribromopyrene as a pale yellow ocher powder.

Next, a mixed solution of 2.0 g of 1,3,6-tribromopyrene, 2.5 g of 4-methylphenylboronic acid, 5.8 g of tripotassium phosphate, 0.88 g of tetrabutylammonium bromide, 61 mg of palladium acetate and 137 ml of deaerated dimethylformamide was heated with stirring under a nitrogen gas flow at 130° C. for 9 hours. After cooling to room temperature, 800 ml of water was injected, followed by extraction with 200 ml of dichloromethane. The organic layer was washed twice with 100 ml of water, dried over magnesium sulfate and then evaporated. The resultant concentrate was purified by silica gel column chromatography and then vacuum-dried to obtain 1.8 g of 1,3,6-tri(4-methylphenyl)pyrene as a pale yellow powder.

Next, a mixed solution of 1.5 g of 1,3,6-tri(4-methylphenyl)pyrene, 0.68 g of N-bromosuccinimide and 30 ml of dimethylformamide was stirred under a nitrogen gas flow at 60° C. for 6 hours. After cooling to room temperature, 50 ml of water was injected, followed by extraction with 100 ml of dichloromethane. The organic layer was washed twice with 50 ml of water, dried over magnesium sulfate and then evaporated. The resultant concentrate was purified by silica gel column chromatography and then vacuum-dried to obtain 1.5 g of 1-bromo-3,6,8-tri(4-methylphenyl)pyrene as a pale yellow powder.

Next, a mixed solution of 1.5 g of 1-bromo-3,6,8-tri(4-methylphenyl)pyrene, 0.66 g of 2-benzofuranboronic acid, 1.74 g of tripotassium phosphate, 73 mg of $PdCl_2(dppf).CH_2Cl_2$ and 30 ml of deaerated dimethylformamide was heated with stirring under a nitrogen gas flow at 100° C. for 4 hours. After cooling to room temperature, 50 ml of water was injected, followed by extraction. The resultant solid was washed with 60 ml of ethanol, recrystallized from toluene and then vacuum-dried to obtain 1.0 g of a yellow crystal. $^1$H-NMR analytical results of the resultant powder as follows and revealed that the orange crystal obtained above is a compound [97].

$^1$H-NMR ($CDCl_3$ (d=ppm)): 2.48-2.50(m, 9H), 7.26-7.71 (m, 17H), 8.01-8.40(m, 5H), 8.75(d, 1H).

This compound [97] was used as a light emitting device material after purification through sublimation under a pressure of $1\times10^{-3}$ Pa at about 250° C. using an oil diffusion pump. HPLC purity (area % at a measuring wavelength of 254 nm) was 99.3% before purification through sublimation and was 99.7% after purification through sublimation.

Example 10

Synthesis of Compound [137]

A mixed solution of 45.0 g of 1-bromopyrene, 21.7 g of 4-methylphenylboronic acid, 34.0 g of tripotassium phosphate, 10.3 g of tetrabutylammonium bromide, 0.71 g of palladium acetate and 1.6 L of dimethylformamide was heated with stirring under a nitrogen gas flow at 120° C. for 5 hours. After cooling to room temperature, 1.6 L of water was injected, followed by stirring at room temperature for 0.5 hours. The precipitated solid was collected by filtration and then washed twice with 200 ml of water. The resultant solid was dissolved in 500 ml of dichloromethane, dried over magnesium sulfate, evaporated and then filtered using Celite. The filtrate was evaporated and the residue was washed twice with 200 ml of methanol. The precipitated solid was collected by filtration and then vacuum-dried to obtain 40.0 g of 1-(4-methylphenyl)pyrene.

Next, a mixed solution of 40.0 g of 1-(4-methylphenyl) pyrene, 24.4 g of N-bromosuccinimide and 1.4 L of dimethylformamide was heated with stirring under a nitrogen gas flow at 40° C. for 7 hours. After cooling the solution to room temperature, 1.0 L of water was injected, followed by extraction with 500 ml of dichloromethane. The organic layer was washed twice with 200 ml of water, dried over magnesium sulfate, evaporated and then filtered using Celite. The filtrate was evaporated and the residue was washed twice with 200 ml of ethyl acetate. The precipitated solid was collected by filtration and then vacuum-dried to obtain 11.4 g of 1-bromo-6-(4-methylphenyl)pyrene.

Next, a mixed solution of 4.6 g of 1-bromo-6-(4-methylphenyl)pyrene, 4.9 g of 2-(3-t-butylphenyl)-4,4,5,5-tetramethyl 1,3,2-dioxaborolane, 8.0 g of tripotassium phosphate, 306 mg of $PdCl_2(dppf).CH_2Cl_2$ and 75 ml of deaerated dimethylformamide was heated with stirring under a nitrogen gas flow at 100° C. for 6 hours. After cooling to room temperature, 100 ml of water was injected, followed by extraction with 100 ml of dichloromethane. The organic layer was washed twice with 50 ml of water, dried over magnesium sulfate and then evaporated. The resultant concentrate was purified by silica gel column chromatography and then vacuum-dried to obtain 4.3 g of 1-(3-t-butylphenyl)-6-(4-methylphenyl)pyrene.

Next, a mixed solution of 4.3 g of 1-(3-t-butylphenyl)-6-(4-methylphenyl)pyrene, 7.3 g of N-bromosuccinimide and 60 ml of dimethylformamide was stirred under a nitrogen gas flow at 90° C. for 7 hours. After cooling to room temperature, 60 ml of water was injected, followed by filtration. The resultant solid was washed with 60 ml of ethanol, recrystallized from 1,3-dimethyl-2-imidazolidinone and then vacuum-dried to obtain 4.4 g of 1,6-dibromo-3-(3-t-butylphenyl)-8-(4-methylphenyl)pyrene.

Next, a mixed solution of 4.4 g of 1,6-dibromo-3-(3-t-butylphenyl)-8-(4-methylphenyl)pyrene, 3.9 g of 2-benzofuranboronic acid, 10.3 g of tripotassium phosphate, 372 mg of $PdCl_2(dppf).CH_2Cl_2$ and 77 ml of deaerated dimethylformamide was heated with stirring under a nitrogen gas flow at 100° C. for 4 hours. After cooling to room temperature, 100 ml of water was injected, followed by filtration. The resultant solid was washed with 60 ml of ethanol, recrystallized from 1,3-dimethyl-2-imidazolidinone and then vacuum-dried to obtain 4.8 g of a yellow crystal. $^1$H-NMR analytical results of the resultant powder as follows and revealed that the yellow crystal obtained above is a compound [137].

$^1$H-NMR (CDCl$_3$ (d=ppm)): 1.44(s, 9H), 2.52(s, 3H), 7.25-7.71(18m, H), 8.27-8.33(m, 2H), 8.43-8.45(m, 2H), 8.79(d, 2H).

This compound [137] was used as a light emitting device material after purification through sublimation under a pressure of $1\times10^{-3}$ Pa at about 260° C. using an oil diffusion pump. HPLC purity (area % at a measuring wavelength of 254 nm) was 99.7% before purification through sublimation and was 99.8% after purification through sublimation.

Example 11

Synthesis of Compound [134]

In the same manner as in Example 10, except that 3-methylphenylboronic acid was used in place of 2-(3-t-butylphenyl)-4,4,5,5-tetramethyl 1,3,2-dioxaborolane, a yellow crystal was obtained. $^1$H-NMR analytical results of the resultant powder as follows and revealed that the yellow crystal obtained above is a compound [134].

$^1$H-NMR (CDCl$_3$ (d=ppm)): 2.52(ss, 6H), 7.27-7.71(18m, H), 8.28-8.33(m, 2H), 8.44(ss, 2H), 8.80(d, 2H).

This compound [134] was used as a light emitting device material after purification through sublimation under a pressure of $1\times10^{-3}$ Pa at about 260° C. using an oil diffusion pump. HPLC purity (area % at a measuring wavelength of 254 nm) was 99.8% before purification through sublimation and was 99.9% after purification through sublimation.

Example 12

Synthesis of Compound [136]

In the same manner as in Example 10, except that 4-t-butylphenylboronic acid was used in place of 2-(3-t-butylphenyl)-4,4,5,5-tetramethyl 1,3,2-dioxaborolane, a yellow crystal was obtained. $^1$H-NMR analytical results of the resultant powder as follows and revealed that the yellow crystal obtained above is a compound [136].

$^1$H-NMR (CDCl$_3$ (d=ppm)): 1.46(s, 9H), 2.52(s, 3H), 7.26-7.71(18m, H), 8.28-8.36(m, 2H), 8.43-8.46(m, 2H), 8.77-8.82(m, 2H).

This compound [136] was used as a light emitting device material after purification through sublimation under a pressure of $1\times10^{-3}$ Pa at about 270° C. using an oil diffusion pump. HPLC purity (area % at a measuring wavelength of 254 nm) was 99.6% before purification through sublimation and was 99.9% after purification through sublimation.

Example 13

Using the compound [14], a light emitting device was produced in the following manner. On a glass substrate measuring 30×40 mm (manufactured by the Asahi Glass Co., 15Ω/□, electron beam evaporated product), an ITO conductive film measuring 150 nm in thickness and 30×13 mm in size was formed in the center of the glass substrate to obtain an anode. The substrate with the anode formed thereon was subjected to ultrasonic washing for 15 minute periods using "Semico-Clean® 56" (manufactured by Furuuchi Chemical Corporation), followed by washing with ultra-pure water. The substrate was subjected to ultrasonic washing for 15 minutes using isopropyl alcohol, dipped in hot methanol for 15 minutes and then dried. Immediately before production of the device, this substrate was subjected to a UV/ozone treatment for one hour and placed in vacuum vapor-deposition equipment, and then the equipment was evacuated until the degree of vacuum inside reached $5\times10^{-5}$ Pa or less.

On the ITO film of the substrate, a 10 nm thick layer of copper phthalocyanine as a hole injecting layer was formed first, and a 50 nm thick layer of 4,4'-bis(N-(1-naphthyl)-N-phenylamino)biphenyl as a hole transporting layer was formed using a resistance heating method. Using H-1 represented by the following formula as a host material and the compound [14] as a dopant material, a 35 nm thick layer of an emissive material having a doping concentration of 2% was formed. Then, a 20 nm thick layer of E-1 represented by the following formula as an electron transporting material was formed. On the organic layer thus formed, a 0.5 nm thick layer of lithium fluoride was formed and then a 1,000 nm thick layer of aluminum was formed as a cathode, and thus a device measuring 5×5 mm was produced. The film thickness is the value displayed by means of a quartz crystal oscillator type film thickness monitor. This light emitting device was subjected to DC driving at 10 mA/cm$^2$. As a result, blue light was emitted at high luminance efficiency of 3.9 m/W. This light emitting device was subjected to continuous DC driving at 10 mA/cm². As a result, a luminance half-decay lifetime was 4,000 hours.

[Chemical Formula 18]

(H-1)

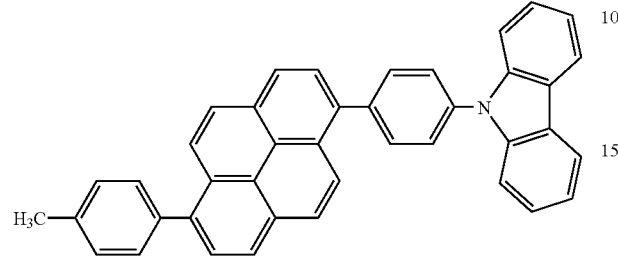

-continued (E-1)

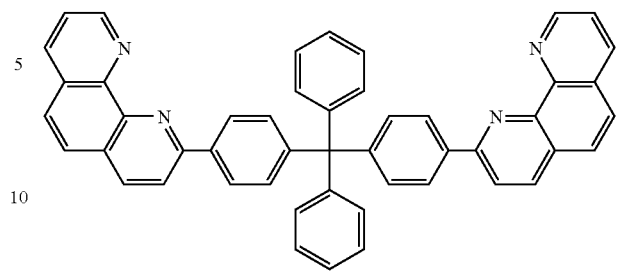

Examples 14 to 23, Comparative Examples 1 to 5

In the same manner as in Example 13, except that materials described in Tables 1 to 2 were used as the dopant material, light emitting devices were produced. The results of the Examples are shown in Tables 1 to 2.

TABLE 1

|  | Emissive layer | | Electron | | Luminous | Luminance half-decay |
|---|---|---|---|---|---|---|
|  | Host material | Dopant material | transporting layer | luminescent color | efficiency (cd/A) | lifetime (h) |
| Example 13 | H-1 | Compound [14] | E-1 | Blue | 3.9 | 4000 |
| Example 14 | H-1 | Compound [1] | E-1 | Blue | 3.0 | 2500 |
| Example 15 | H-1 | Compound [13] | E-1 | Blue | 3.5 | 3200 |
| Example 16 | H-1 | Compound [19] | E-1 | Blue | 3.8 | 3600 |
| Example 17 | H-1 | Compound [36] | E-1 | Blue | 3.9 | 3300 |
| Comparative Example 1 | H-1 | D-1 | E-1 | Blue | 1.6 | 600 |
| Comparative Example 2 | H-1 | D-2 | E-1 | Blue | 1.1 | 300 |
| Comparative Example 3 | H-1 | D-3 | E-1 | Blue | 2.9 | 500 |

TABLE 2

|  | Emissive layer | | Electron | | Luminous | |
|---|---|---|---|---|---|---|
|  | Host material | Dopant material | transporting layer | luminescent color | efficiency (cd/A) | C.I.E (x, y) |
| Example 18 | H-1 | Compound [61] | E-1 | Blue | 3.0 | (0.15, 0.10) |
| Example 19 | H-1 | Compound [156] | E-1 | Blue | 3.1 | (0.15, 0.23) |
| Example 20 | H-1 | Compound [79] | E-1 | Blue | 3.6 | (0.15, 0.12) |
| Example 21 | H-1 | Compound [87] | E-1 | Blue | 3.6 | (0.15, 0.12) |
| Example 22 | H-1 | Compound [97] | E-1 | Blue | 3.9 | (0.15, 0.20) |
| Example 23 | H-1 | Compound [109] | E-1 | Blue | 2.8 | (0.15, 0.14) |
| Comparative Example 4 | H-1 | D-1 | E-1 | Blue | 1.6 | (0.15, 0.18) |
| Comparative Example 5 | H-1 | D-3 | E-1 | Blue | 2.9 | (0.18, 0.38) |

D-1 to D-3 in Table 2 are compounds represented by the following formulas.

[Chemical Formula 19]

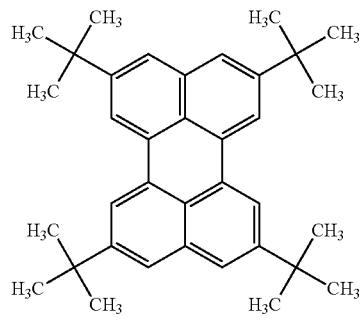
(D-1)

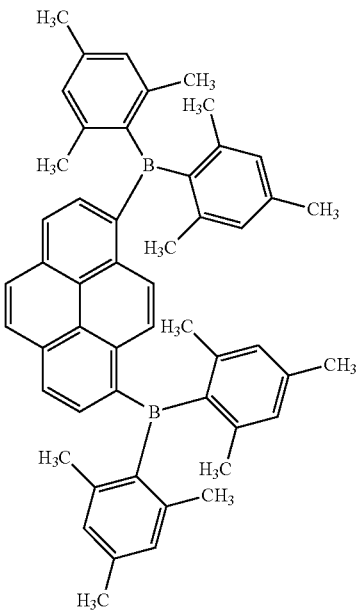
(D-2)

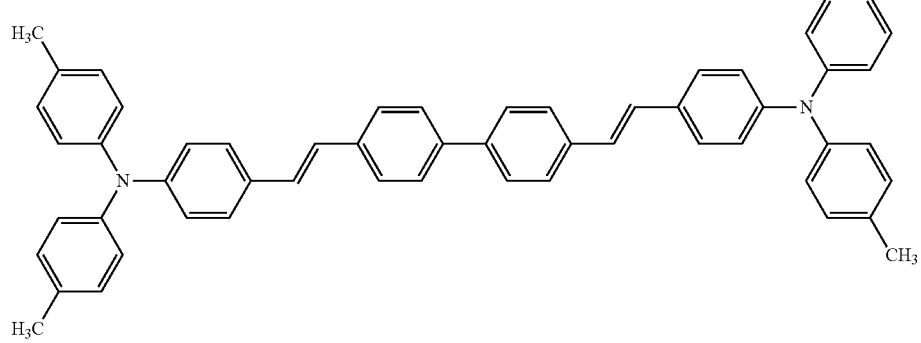
(D-3)

Examples 24 to 27

In the same manner as in Example 13, except that materials described in Table 3 were used as the host material, light emitting devices were produced. The results of the Examples are shown in Table 3.

TABLE 3

| Emissive layer | | Electron transporting layer | luminescent color | Luminous efficiency (cd/A) | Luminance half-decay lifetime (h) |
| --- | --- | --- | --- | --- | --- |
| Host material | Dopant material | | | | |
| Example 24 H-2 | Compound [14] | E-1 | Blue | 3.6 | 3600 |
| Example 25 H-3 | Compound [14] | E-1 | Blue | 3.4 | 3500 |

TABLE 3-continued

|  | Emissive layer | | Electron transporting layer | Luminescent color | Luminous efficiency (cd/A) | C.I.E (x, y) |
|---|---|---|---|---|---|---|
|  | Host material | Dopant material | | | | |
| Example 26 | H-2 | Compound [79] | E-1 | Blue | 3.4 | (0.15, 0.12) |
| Example 27 | H-3 | Compound [79] | E-1 | Blue | 3.3 | (0.15, 0.13) |

H-2 to H-3 in Table 3 are compounds represented by the following formulas.

[Chemical Formula 20]

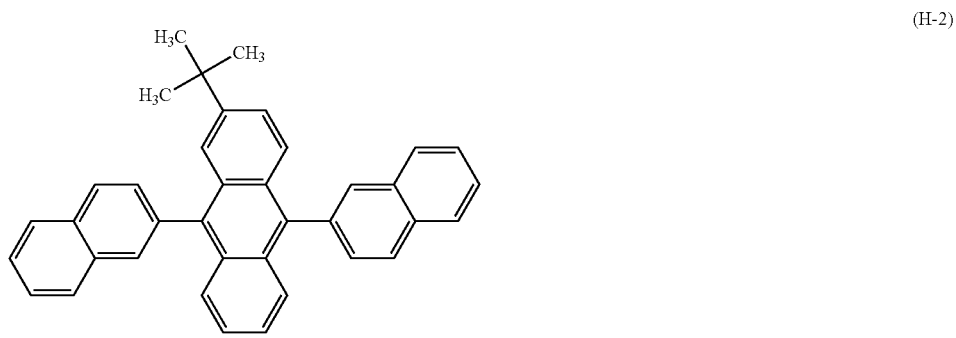

(H-2)

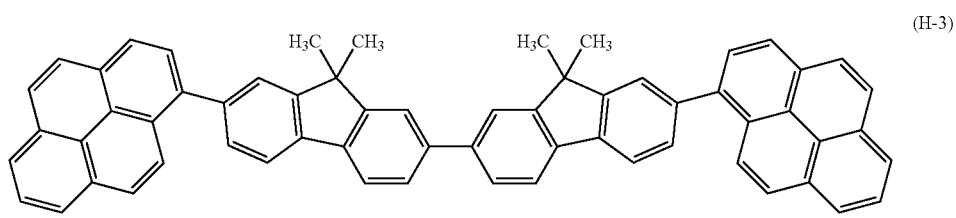

(H-3)

Examples 28 to 34

In the same manner as in Example 13, except that materials described in Table 4 were used as the electron transporting material, light emitting devices were produced. The results of the Examples are shown in Table 4.

TABLE 4

|  | Emissive layer | | Electron transporting layer | luminescent color | Luminous efficiency (cd/A) | Luminance half-decay lifetime (h) |
|---|---|---|---|---|---|---|
|  | Host material | Dopant material | | | | |
| Example 28 | H-1 | Compound [14] | E-2 | Blue | 4.0 | 4500 |
| Example 29 | H-1 | Compound [14] | E-3 | Blue | 2.3 | 3800 |
| Example 30 | H-1 | Compound [14] | E-4 | Blue | 3.8 | 4000 |
| Example 31 | H-1 | Compound [14] | E-5 | Blue | 3.9 | 3500 |
| Example 32 | H-1 | Compound [14] | E-6 | Blue | 3.8 | 4300 |
| Example 33 | H-1 | Compound [14] | E-7 | Blue | 3.8 | 4000 |
| Example 34 | H-1 | Compound [14] | E-8 | Blue | 3.3 | 3800 |

E-2 to E-8 in Table 4 are compounds represented by the following formulas.

[Chemical Formula 21]

(E-2)
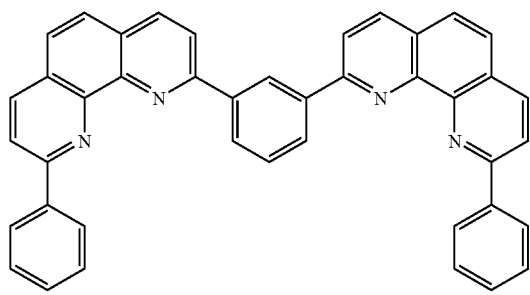

(E-3)
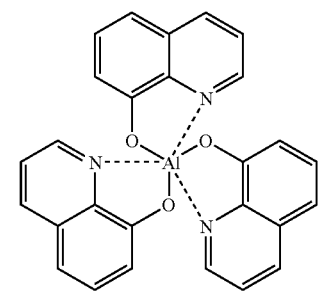

(E-4)
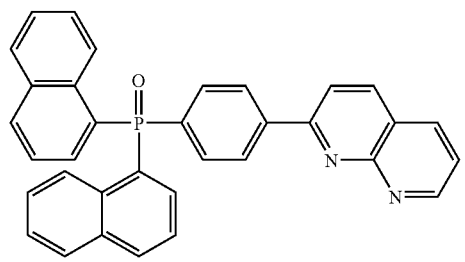

(E-5)
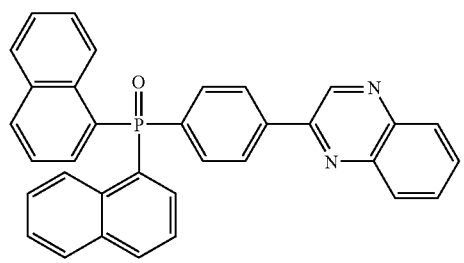

(E-6)
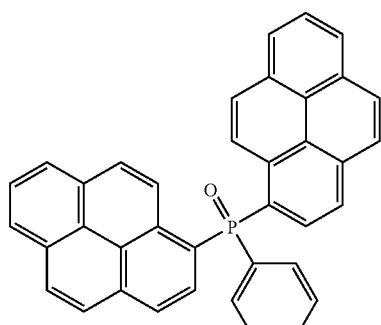

(E-7)
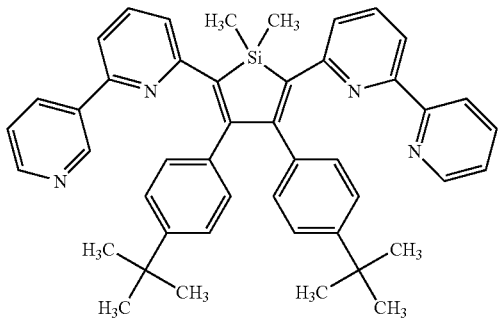

(E-8)
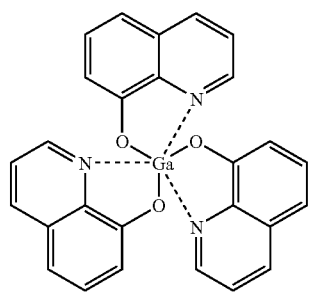

Example 35

In the same manner as in Example 13, except that the compound [137] was used as the dopant material in the doping concentration of 2%, a light emitting device was produced. This light emitting device was subjected to Dc driving at 10 mA/cm². As a result, light was emitted at high luminance efficiency of 5.2 lm/W and green light having high chromatic purity in terms of C.I.E chromaticity coordinate of (0.34, 0.66) was emitted.

Example 36

In the same manner as in Example 13, except that the compound [134] was used as the dopant material in the doping concentration of 2%, a light emitting device was produced. This light emitting device was subjected to Dc driving at 10 mA/cm². As a result, light was emitted at high luminance efficiency of 5.8 lm/W and green light having high chromatic purity in terms of C.I.E chromaticity coordinate of (0.35, 0.65) was emitted.

Example 37

In the same manner as in Example 13, except that the compound [136] was used as the dopant material in the doping concentration of 2%, a light emitting device was produced. This light emitting device was subjected to Dc driving at 10 mA/cm². As a result, light was emitted at high luminance efficiency of 6.0 lm/W and green light having high chromatic purity in terms of C.I.E chromaticity coordinate of (0.34, 0.66) was emitted.

Example 38

The light emitting device was formed in the same manner as in Example 13, except that after depositing an emissive material using H-1 as a host material and D-3 as a dopant material to form a 5 nm thick layer having a doping concentration of 5%, a further emissive material using H-1 as a host material and the compound [14] as a dopant material was laminated to a thickness of 30 nm having a doping concentration of 2%. This light emitting device was subjected to Dc driving at 10 mA/cm². As a result, white light was emitted at high luminance efficiency of 6.2 lm/W. This light emitting device was subjected to continuous DC driving at 10 mA/cm². As a result, a luminance half-decay lifetime was 10,000 hours.

Example 39

On a glass substrate measuring 30×40 mm (manufactured by the Asahi Glass Co., 15Ω/□, electron beam evaporated product), an ITO conductive film measuring 150 nm in thickness and 30×13 mm in size was formed in the center of the glass substrate to obtain an anode. The substrate with the anode formed thereon was subjected to ultrasonic washing for 15 minute periods using "Semico-Clean® 56" (manufactured by Furuuchi Chemical Corporation), followed by washing with ultra-pure water. The substrate was subjected to ultrasonic washing for 15 minutes using isopropyl alcohol, dipped in hot methanol for 15 minutes and then dried. Immediately before production of the device, this substrate was subjected to a UV/ozone treatment for one hour and placed in vacuum vapor-deposition equipment, and then the equipment was evacuated until the degree of vacuum inside reached $5 \times 10^{-4}$ Pa or less.

On the ITO film of the substrate, a 150 nm thick layer of 4,4'-bis(N-(m-tolyl)-N-phenylamino)biphenyl as a hole transporting layer was formed first using a resistance heating method. Using H-1 as a host material and the compound [79] as a dopant material, a 35 nm thick layer having a doping concentration of 2% was formed. Then, a 20 nm thick layer of E-1 as an electron transporting material was formed. The film thickness is the value displayed by means of a quartz crystal oscillator type film thickness monitor. Then, under vacuum, mask exchange was performed with a mask comprising a kovar sheet of thickness 50 μm in which sixteen 250 μm apertures (remaining width 50 μm, corresponding to a 300 μm pitch) had been provided by wet etching, so as to intersect the ITO stripes at right angles, and this then fixed with a magnet from the underside so that the mask and ITO substrate closely adhered. After doping the organic layer with 0.5 nm of lithium, there was vapor-deposited 200 nm of aluminum and a 32×16 dot matrix device produced. This device was subjected to matrix driving and, as a result, character display was possible without cross-talk.

Industrial Applicability

The light emitting device material of the present invention can provide a light emitting device material which can be used for a light emitting device and is excellent in fluorescence quantum yield. According to the present invention, a light emitting device which has high luminance efficiency and is also excellent in chromatic purity and durability. The light emitting device of the present invention can be used for display elements, flat panel displays, backlights, lighting, interiors, marks, signboards, electronic cameras, light signal generators and the like.

The invention claimed is:

1. A light emitting device material containing a pyrene compound represented by formula (1):

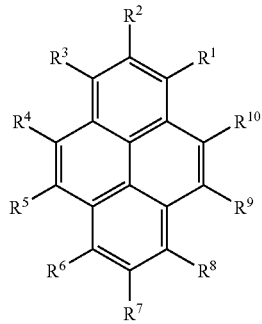

wherein $R^1$ to $R^{10}$ may be the same or different and represent a group selected from the group consisting of hydrogen, an alkyl group, a cycloalkyl group, a heterocyclic group, an alkenyl group, a cycloalkenyl group, an alkynyl group, an alkoxy group, an alkylthio group, an arylether group, an arylthioether group, an aryl group, a heteroaryl group, halogen, an amino group, a cyano group, a silyl group and —P(=O)—$R^{11}$, and adjacent substituents may be combined to form a ring structure; $R^{11}$ represents a group selected from among an aryl group and a heteroaryl group, provided that any one of $R^1$ to $R^{10}$ is a group represented by formula (2) and the pyrene compound contains only one group represented by formula (2):

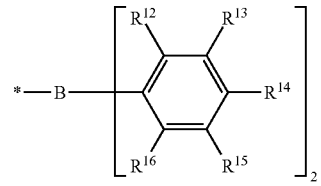

wherein $R^{12}$ to $R^{16}$ may be the same or different and represent a group selected from the group consisting of hydrogen, an alkyl group, a cycloalkyl group, a heterocyclic group, an alkenyl group, a cycloalkenyl group, an alkynyl group, an alkoxy group, an alkylthio group, an arylether group, an arylthioether group, an aryl group, a heteroaryl group, halogen, an amino group, a cyano group and a silyl group, and adjacent substituents may be combined to form a ring structure, and B is a boron atom, wherein at least one of $R^1$ to $R^{10}$ is an alkyl group or an aryl group.

2. The light emitting device material according to claim 1, wherein any one of $R^1$, $R^3$, $R^6$ and $R^8$ is a substituent represented by the general formula (2).

3. The light emitting device material according to claim 1, wherein $R^{12}$, $R^{14}$ and $R^{16}$ is a methyl group.

4. The light emitting device material according to claim 1, wherein $R^1$ is a substituent represented by formula (2) and $R^6$ or $R^8$ is an aryl group or a heteroaryl group.

5. The light emitting device material according to claim 4, wherein $R^3$ and $R^8$ is an aryl group or a heteroaryl group.

6. A light emitting device comprising an anode, a cathode, and an organic layer which exists between the anode and the cathode, wherein the organic layer contains at least an emissive layer, the emissive layer emits light by means of electrical energy, and the organic layer contains the light emitting device material according to claim 1.

7. The light emitting device according to claim 6, wherein the emissive layer contains a host material and a dopant material, and the dopant material is a pyrene compound represented by the general formula (1).

8. The light emitting device according to claim 6 or 7 wherein an electron transporting layer further exists between the emissive layer and the cathode, and the electron transporting layer contains an electron-accepting nitrogen and also contains a compound having a heteroaryl ring structure composed of an element selected from carbon, hydrogen, nitrogen, oxygen, silicon and phosphorus.

9. A light emitting device material containing a pyrene compound represented by formula (1):

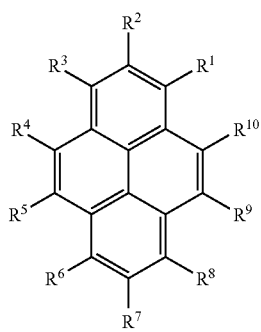

(1)

wherein $R^1$ is a substituent represented by formula (3), each of $R^3$ and $R^8$ are an aryl group or a heteroaryl group and each of $R^2$, $R^4$ $R^5$, $R^6$, $R^7$, $R^9$ and $R^{10}$ is hydrogen;

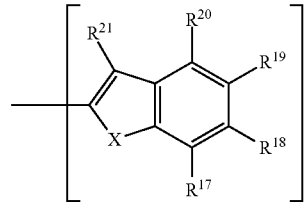

(3)

wherein $R^{17}$ to $R^{21}$ may be the same or different and represent a group selected from the group consisting of hydrogen, an alkyl group, a cycloalkyl group, a heterocyclic group, an alkenyl group, a cycloalkenyl group, an alkynyl group, an alkoxy group, an alkylthio group, an arylether group, an arylthioether group, an aryl group, a heteroaryl group, halogen, an amino group, a cyano group and a silyl group, X is a group selected from among an oxygen atom, a sulfur atom and —$NR^{22}$—, $R^{22}$ is a group selected from among hydrogen, an alkyl group, a cycloalkyl group, a heterocyclic group, an alkenyl group, a cycloalkenyl group, an alkynyl group, an aryl group, a heteroaryl group and an amino group, and $R^{22}$ and $R^{17}$ may be combined to form a ring.

10. The light emitting device material according to claim 9, wherein X is an oxygen atom.

11. A light emitting device comprising an anode, a cathode, and an organic layer which exists between the anode and the cathode, wherein the organic layer contains at least an emissive layer, the emissive layer emits light by means of electrical energy, and the organic layer contains the light emitting device material according to claim 9.

12. The light emitting device according to claim 11, wherein the emissive layer contains a host material and a dopant material, and the dopant material is a pyrene compound represented by the general formula (1).

13. The light emitting device according to claim 11, wherein an electron transporting layer further exists between the emissive layer and the cathode, and the electron transporting layer contains an electron-accepting nitrogen and also contains a compound having a heteroaryl ring structure composed of an element selected from carbon, hydrogen, nitrogen, oxygen, silicon and phosphorus.

14. A light emitting device material containing a pyrene compound represented by the formula (1):

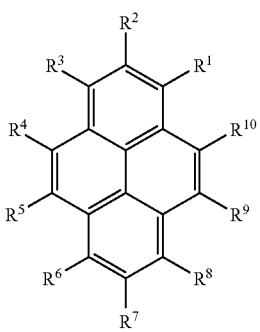

(1)

wherein $R^1$ and $R^6$ are substituents represented by formula (3), each of $R^3$ and $R^8$ is an aryl group and each of $R^2$, $R^4$, $R^5$, $R^7$, $R^9$ and $R^{10}$ is hydrogen:

(3)

wherein $R^{17}$ to $R^{21}$ may be the same or different and represent a group selected from the group consisting of hydrogen, an alkyl group, a cycloalkyl group, a heterocyclic group, an alkenyl group, a cycloalkenyl group, an alkynyl group, an alkoxy group, an alkylthio group, an arylether group, an arylthioether group, an aryl group, a heteroaryl group, halogen, an amino group, a cyano group and a silyl group, X is a group selected from among an oxygen atom, a sulfur atom and —$NR^{22}$—, $R^{22}$ is a group selected from among hydrogen, an alkyl group, a cycloalkyl group, a heterocyclic group, an alkenyl group, a cycloalkenyl group, an alkynyl group, an aryl group, a heteroaryl group and an amino group, and $R^{22}$ and $R^{17}$ may be combined to form a ring.

15. The light emitting device material according to claim 14, wherein X is an oxygen atom.

16. A light emitting device comprising an anode, a cathode, and an organic layer which exists between the anode and the cathode, wherein the organic layer contains at least an emissive layer, the emissive layer emits light by means of electrical energy, and the organic layer contains the light emitting device material according to claim 14.

17. The light emitting device according to claim 16, wherein the emissive layer contains a host material and a dopant material, and the dopant material is a pyrene compound represented by the general formula (1).

18. The light emitting device according to claim 16, wherein an electron transporting layer further exists between the emissive layer and the cathode, and the electron transporting layer contains an electron-accepting nitrogen and also contains a compound having a heteroaryl ring structure composed of an element selected from carbon, hydrogen, nitrogen, oxygen, silicon and phosphorus.

* * * * *